US009962276B2

(12) United States Patent
Quijano et al.

(10) Patent No.: US 9,962,276 B2
(45) Date of Patent: May 8, 2018

(54) INTRAGASTRIC SPACE FILLER

(71) Applicant: ReShape Medical, Inc., San Clemente, CA (US)

(72) Inventors: Rodolfo C. Quijano, Laguna Hills, CA (US); Hosheng Tu, Newport Beach, CA (US); Andrew H. Cragg, Edina, MN (US); Bobby Purkait, Santa Barbara, CA (US)

(73) Assignee: ReShape Medical LLC, St. Paul, MN (US)

( * ) Notice: Subject to any disclaimer, the term of this patent is extended or adjusted under 35 U.S.C. 154(b) by 0 days. days.

(21) Appl. No.: 13/858,767

(22) Filed: Apr. 8, 2013

(65) Prior Publication Data

US 2013/0296914 A1 Nov. 7, 2013

Related U.S. Application Data

(63) Continuation of application No. 11/263,302, filed on Oct. 31, 2005, now abandoned.

(51) Int. Cl.
*A61F 5/00* (2006.01)

(52) U.S. Cl.
CPC .......... *A61F 5/0036* (2013.01); *A61F 5/003* (2013.01)

(58) Field of Classification Search
CPC ...... A61F 5/0033; A61F 5/0036; A61F 5/004; A61F 5/0046
USPC ........................................................ 606/192
See application file for complete search history.

(56) References Cited

U.S. PATENT DOCUMENTS

| 1,666,690 | A | 4/1928 | Drevitson |
| 1,690,995 | A | 11/1928 | Pratt |
| 2,493,326 | A | 1/1950 | Trinder |
| 2,579,301 | A | 12/1951 | Buntin |
| 3,131,867 | A | 5/1964 | Miller et al. |
| 4,198,983 | A | 4/1980 | Becker et al. |
| 4,356,824 | A | 11/1982 | Vazquez |
| 4,368,739 | A | 1/1983 | Nelson, Jr. |
| 4,436,087 | A | 3/1984 | Ouchi |
| 4,465,072 | A | 8/1984 | Taheri |
| 4,465,818 | A | 8/1984 | Shirahata et al. |
| 4,485,805 | A | 12/1984 | Foster, Jr. |
| 4,543,089 | A | 9/1985 | Moss |
| 4,598,699 | A | 7/1986 | Garren et al. |
| 4,723,547 | A | 2/1988 | Kullas et al. |

(Continued)

FOREIGN PATENT DOCUMENTS

| CA | 2638988 | 5/2007 |
| DE | 8708978 U1 | 11/1987 |

(Continued)

OTHER PUBLICATIONS

International Search Report; International Application No. PCT/US2008/058677, Applicant: ReShape Medical et al., dated Aug. 21, 2008, 12 pages.

(Continued)

*Primary Examiner* — Diane Yabut
(74) *Attorney, Agent, or Firm* — Merchant & Gould P.C.

(57) ABSTRACT

A gastric space filler device for treating obesity in a patient by reducing the stomach volume comprising an inflatable space filler and a safety element secured to the space filler, wherein the safety element yields a noticeable signal for causing removal of the space filler.

39 Claims, 14 Drawing Sheets

(56) References Cited

U.S. PATENT DOCUMENTS

| | | | |
|---|---|---|---|
| 4,739,758 A | 4/1988 | Lai et al. |
| 4,763,653 A | 8/1988 | Rockey |
| 4,940,458 A | 7/1990 | Cohn |
| 5,073,347 A | 12/1991 | Martirosian et al. |
| 5,084,061 A | 1/1992 | Gau et al. |
| 5,123,840 A | 6/1992 | Nates |
| 5,224,626 A | 7/1993 | Hernandez |
| 5,234,454 A | 8/1993 | Bangs |
| 5,259,399 A | 11/1993 | Brown |
| 5,263,934 A | 11/1993 | Haak |
| 5,273,536 A | 12/1993 | Savas |
| 5,318,530 A | 6/1994 | Nelson, Jr. |
| 5,334,187 A | 8/1994 | Fischell et al. |
| 5,378,530 A | 1/1995 | Metivaud et al. |
| 5,431,173 A | 7/1995 | Chin et al. |
| 5,496,271 A | 3/1996 | Burton et al. |
| 5,516,812 A | 5/1996 | Chu et al. |
| 5,575,772 A | 11/1996 | Lennox |
| 5,639,810 A | 6/1997 | Smith, III et al. |
| 5,643,209 A | 7/1997 | Fugoso et al. |
| 5,713,486 A | 2/1998 | Beech |
| 5,730,722 A | 3/1998 | Wilk |
| 5,779,728 A | 7/1998 | Lunsford et al. |
| 5,857,991 A | 1/1999 | Grothoff et al. |
| 5,876,376 A | 3/1999 | Schwab et al. |
| 5,904,701 A * | 5/1999 | Daneshvar ............. A61B 17/24 128/DIG. 25 |
| 5,938,669 A | 8/1999 | Klaiber et al. |
| 5,976,073 A | 11/1999 | Ouchi |
| 5,993,473 A | 11/1999 | Chan et al. |
| 5,997,503 A | 12/1999 | Willis et al. |
| 6,050,274 A | 4/2000 | Gelardi et al. |
| 6,149,621 A | 11/2000 | Makihara |
| 6,179,878 B1 | 1/2001 | Duerig et al. |
| 6,254,355 B1 | 7/2001 | Gharib |
| 6,276,567 B1 | 8/2001 | Diaz et al. |
| 6,280,411 B1 | 8/2001 | Lennox |
| 6,283,951 B1 | 9/2001 | Flaherty et al. |
| 6,423,058 B1 | 7/2002 | Edwards et al. |
| 6,427,089 B1 * | 7/2002 | Knowlton ............... 607/101 |
| 6,453,907 B1 | 9/2002 | Forsell |
| 6,454,785 B2 | 9/2002 | De Hoyos Garza |
| 6,524,234 B2 | 2/2003 | Ouchi |
| 6,535,764 B2 | 3/2003 | Imran et al. |
| 6,540,789 B1 | 4/2003 | Silverman et al. |
| 6,547,788 B1 | 4/2003 | Maguire et al. |
| 6,579,301 B1 * | 6/2003 | Bales et al. ............ 606/191 |
| 6,592,552 B1 | 7/2003 | Schmidt |
| 6,613,018 B2 | 9/2003 | Bagga et al. |
| 6,613,037 B2 | 9/2003 | Khosravi et al. |
| 6,689,051 B2 | 2/2004 | Nakada |
| 6,706,010 B1 | 3/2004 | Miki et al. |
| 6,826,428 B1 | 11/2004 | Chen et al. |
| 6,850,128 B2 | 2/2005 | Park |
| 6,866,627 B2 | 3/2005 | Nozue |
| 6,866,657 B2 | 3/2005 | Shchervinsky |
| 6,869,431 B2 | 3/2005 | Maguire et al. |
| 6,890,346 B2 | 5/2005 | Ganz et al. |
| 6,902,535 B2 | 6/2005 | Eberhart et al. |
| 6,923,754 B2 | 8/2005 | Lubock |
| 6,931,286 B2 | 8/2005 | Sigg et al. |
| 6,942,680 B2 | 9/2005 | Grayzel et al. |
| 6,958,052 B1 | 10/2005 | Charlton |
| 7,001,419 B2 | 2/2006 | DiCaprio et al. |
| 7,016,735 B2 | 3/2006 | Imran et al. |
| 7,020,531 B1 | 3/2006 | Colliou et al. |
| 7,033,373 B2 | 4/2006 | de la Torre et al. |
| 7,056,305 B2 | 6/2006 | Garza Alvarez |
| 7,076,305 B2 | 7/2006 | Imran et al. |
| 7,081,125 B2 | 7/2006 | Edwards et al. |
| 7,131,945 B2 | 11/2006 | Fink et al. |
| 7,483,746 B2 | 1/2009 | Lee et al. |
| 7,625,355 B2 | 12/2009 | Yu et al. |
| 7,749,254 B2 | 7/2010 | Sobelman et al. |
| 7,829,572 B2 | 11/2010 | Didiuk et al. |
| 7,931,693 B2 | 4/2011 | Binmoeller et al. |
| 8,083,757 B2 | 12/2011 | Gannoe et al. |
| 8,556,925 B2 | 10/2013 | Makower et al. |
| 8,840,952 B2 | 9/2014 | Ashby et al. |
| 8,894,568 B2 | 11/2014 | Pecor et al. |
| 9,050,174 B2 | 6/2015 | Pecor et al. |
| 9,149,611 B2 | 10/2015 | Bouasaysy et al. |
| 2001/0022988 A1 * | 9/2001 | Schwarz et al. ............ 427/2.1 |
| 2001/0037127 A1 | 11/2001 | De Hoyos Garza |
| 2002/0055757 A1 | 5/2002 | Torre et al. |
| 2002/0161388 A1 | 10/2002 | Samuels et al. |
| 2002/0173804 A1 | 11/2002 | Rousseau |
| 2003/0105800 A1 | 6/2003 | Cullen |
| 2003/0114878 A1 | 6/2003 | Diederich et al. |
| 2003/0187390 A1 | 10/2003 | Bates et al. |
| 2004/0044354 A1 | 3/2004 | Gannoe et al. |
| 2004/0059289 A1 | 3/2004 | Garza Alvarez |
| 2004/0073162 A1 | 4/2004 | Bleam et al. |
| 2004/0087902 A1 | 5/2004 | Richter |
| 2004/0093058 A1 | 5/2004 | Cottone et al. |
| 2004/0106899 A1 | 6/2004 | McMichael et al. |
| 2004/0116897 A1 | 6/2004 | Aboul-Hosn |
| 2004/0186503 A1 | 9/2004 | Delegge |
| 2004/0199196 A1 | 10/2004 | Ravo |
| 2004/0254600 A1 | 12/2004 | Zarbatany et al. |
| 2005/0038415 A1 | 2/2005 | Rohr et al. |
| 2005/0055039 A1 | 3/2005 | Burnett et al. |
| 2005/0059990 A1 | 3/2005 | Ayala et al. |
| 2005/0075624 A1 | 4/2005 | Miesel |
| 2005/0085792 A1 | 4/2005 | Gershowitz |
| 2005/0119674 A1 | 6/2005 | Gingras |
| 2005/0131442 A1 | 6/2005 | Yachia et al. |
| 2005/0143784 A1 * | 6/2005 | Imran ............... 607/40 |
| 2005/0159769 A1 | 7/2005 | Alverdy |
| 2005/0177103 A1 | 8/2005 | Hunter et al. |
| 2005/0192614 A1 | 9/2005 | Binmoeller |
| 2005/0192615 A1 | 9/2005 | Torre et al. |
| 2005/0203563 A9 | 9/2005 | Pederson, Jr. et al. |
| 2005/0228504 A1 | 10/2005 | Demarais |
| 2005/0267595 A1 | 12/2005 | Chen et al. |
| 2005/0267596 A1 * | 12/2005 | Chen et al. ............ 623/23.67 |
| 2005/0273060 A1 * | 12/2005 | Levy ............... A61B 17/1114 604/192 |
| 2006/0025799 A1 | 2/2006 | Baso |
| 2006/0058829 A1 | 3/2006 | Sampson et al. |
| 2006/0095032 A1 | 5/2006 | Jackson et al. |
| 2006/0135984 A1 | 6/2006 | Kramer et al. |
| 2006/0142700 A1 | 6/2006 | Sobelman et al. |
| 2006/0178691 A1 | 8/2006 | Binmoeller |
| 2006/0235448 A1 | 10/2006 | Roslin et al. |
| 2006/0270906 A1 | 11/2006 | Matsuno |
| 2006/0271088 A1 * | 11/2006 | Alfrhan ............... A61F 5/0043 606/192 |
| 2006/0293647 A1 | 12/2006 | McRae et al. |
| 2007/0016262 A1 * | 1/2007 | Gross et al. ............ 607/40 |
| 2007/0078476 A1 * | 4/2007 | Hull et al. ............ 606/191 |
| 2007/0083224 A1 | 4/2007 | Hively |
| 2007/0093728 A1 | 4/2007 | Douglas et al. |
| 2007/0100367 A1 | 5/2007 | Quijano et al. |
| 2007/0100368 A1 | 5/2007 | Quijano et al. |
| 2007/0100369 A1 | 5/2007 | Cragg et al. |
| 2007/0118168 A1 | 5/2007 | Lointier et al. |
| 2007/0135829 A1 | 6/2007 | Paganon et al. |
| 2007/0142770 A1 | 6/2007 | Rioux et al. |
| 2007/0149994 A1 | 6/2007 | Sosnowski et al. |
| 2007/0173881 A1 | 7/2007 | Birk et al. |
| 2007/0233161 A1 | 10/2007 | Weller et al. |
| 2007/0250020 A1 | 10/2007 | Kim et al. |
| 2007/0265369 A1 | 11/2007 | Muratoglu et al. |
| 2008/0082056 A1 | 4/2008 | Mauch et al. |
| 2008/0097513 A1 | 4/2008 | Kaji et al. |
| 2008/0119729 A1 | 5/2008 | Copa et al. |
| 2008/0172079 A1 | 7/2008 | Birk |
| 2008/0208135 A1 | 8/2008 | Annunziata et al. |
| 2008/0208241 A1 | 8/2008 | Weiner et al. |
| 2008/0233167 A1 | 9/2008 | Li et al. |
| 2008/0243071 A1 | 10/2008 | Quijano et al. |
| 2008/0243166 A1 | 10/2008 | Paganon et al. |
| 2008/0312679 A1 | 12/2008 | Hardert et al. |

(56) References Cited

U.S. PATENT DOCUMENTS

| | | |
|---|---|---|
| 2008/0319471 A1 | 12/2008 | Sosnowski et al. |
| 2009/0048624 A1 | 2/2009 | Alverdy |
| 2009/0082623 A1 | 3/2009 | Rothe et al. |
| 2009/0259236 A2 | 10/2009 | Burnett et al. |
| 2009/0287231 A1 | 11/2009 | Brooks et al. |
| 2010/0049224 A1 | 2/2010 | Vargas |
| 2010/0063530 A1 | 3/2010 | Valencon et al. |
| 2010/0130998 A1 | 5/2010 | Alverdy |
| 2010/0174307 A1 | 7/2010 | Birk et al. |
| 2010/0191270 A1 | 7/2010 | Garza et al. |
| 2010/0234853 A1 | 9/2010 | Pecor et al. |
| 2010/0251837 A1 | 10/2010 | Bouasaysy et al. |
| 2011/0172767 A1 | 7/2011 | Rathi et al. |
| 2011/0276076 A1 | 11/2011 | Paganon |
| 2011/0295300 A1 | 12/2011 | Verd et al. |
| 2012/0191126 A1 | 7/2012 | Pecor et al. |
| 2012/0271336 A1 | 10/2012 | Hamman et al. |
| 2012/0271338 A1 | 10/2012 | Bouasaysy et al. |
| 2012/0289992 A1 | 11/2012 | Quijano et al. |
| 2013/0035710 A1 | 2/2013 | Bouasaysy et al. |
| 2013/0053880 A1 | 2/2013 | Bouasaysy et al. |
| 2013/0060274 A1 | 3/2013 | Bouasaysy et al. |
| 2013/0102876 A1 | 4/2013 | Limon et al. |
| 2013/0261654 A1 | 10/2013 | Bouasaysy et al. |
| 2013/0296914 A1 | 11/2013 | Quijano et al. |
| 2014/0031850 A1 | 1/2014 | Bouasaysy et al. |
| 2014/0257358 A1 | 9/2014 | Alverdy et al. |
| 2014/0371775 A1 | 12/2014 | Ashby et al. |
| 2015/0216529 A1 | 8/2015 | Kwok et al. |
| 2015/0238342 A1 | 8/2015 | Sosnowski et al. |
| 2015/0265811 A1 | 9/2015 | Pecor |
| 2015/0366691 A1 | 12/2015 | Bouasaysy et al. |
| 2016/0008156 A1 | 1/2016 | Pecor et al. |

FOREIGN PATENT DOCUMENTS

| | | |
|---|---|---|
| EP | 0103481 | 3/1984 |
| EP | 103481 A1 | 3/1984 |
| EP | 0457456 A1 | 11/1991 |
| EP | 0485903 A2 | 5/1992 |
| EP | 1781183 | 5/2007 |
| EP | 1781183 B1 | 4/2013 |
| FR | 2862525 A1 | 5/2005 |
| FR | 2892297 | 4/2007 |
| FR | 2892297 A1 | 4/2007 |
| GB | 2090747 A | 7/1982 |
| GB | 2139902 A | 11/1984 |
| JP | S57168674 | 10/1982 |
| JP | S6415063 | 1/1989 |
| JP | H091872 | 4/1989 |
| JP | H08322943 | 12/1996 |
| JP | 2001128985 | 5/2001 |
| JP | 2006333888 | 12/2006 |
| JP | 2009285135 A | 12/2009 |
| JP | 2015154964 | 8/2015 |
| JP | 2016127954 | 7/2016 |
| WO | 8805671 A1 | 8/1988 |
| WO | 9000369 A1 | 1/1990 |
| WO | 9925418 A1 | 5/1999 |
| WO | 0141700 A1 | 6/2001 |
| WO | WO-2001041700 | 6/2001 |
| WO | WO-0166166 A2 | 9/2001 |
| WO | 0240081 A2 | 5/2002 |
| WO | WO-2002040081 | 5/2002 |
| WO | 2005082296 A1 | 9/2005 |
| WO | 2005107641 A2 | 11/2005 |
| WO | 2005120363 A1 | 12/2005 |
| WO | WO-2006035446 A2 | 4/2006 |
| WO | WO-2006056944 A1 | 6/2006 |
| WO | WO-2006/128978 A1 | 12/2006 |
| WO | WO-2007027812 A2 | 3/2007 |
| WO | WO-2007053556 A1 | 5/2007 |
| WO | WO-2007053706 A1 | 5/2007 |
| WO | WO-2007053707 A1 | 5/2007 |
| WO | WO-2007075810 A1 | 7/2007 |
| WO | WO-2008042819 A2 | 4/2008 |
| WO | WO-2008121831 A1 | 10/2008 |
| WO | WO-2009112786 A2 | 9/2009 |
| WO | 2010048021 A2 | 4/2010 |
| WO | WO-2010048021 | 4/2010 |
| WO | WO-2010115161 A2 | 10/2010 |
| WO | WO-2011011629 A2 | 1/2011 |
| WO | WO-2011011741 A2 | 1/2011 |
| WO | WO-2011011743 A2 | 1/2011 |
| WO | WO-2011038270 A2 | 3/2011 |
| WO | WO-2012048226 A1 | 4/2012 |

OTHER PUBLICATIONS

International Search Report; International Application No. PCT/US2006/042710, Applicant: Abdominus, Inc. et al., dated Mar. 15, 2007, 9 pages.
International Search Report; International Application No. PCT/US2006/048647, Applicant: Abdominus, Inc. et al., dated May 22, 2007, 12 pages.
International Search Report; International Application No. PCT/US2008/068058, Applicant: ReShape Medical, Inc. et al, dated Nov. 19, 2008, 11 pages.
International Search Report; International Application No. PCT/US2006/042711, Applicant: Abdominus, Inc. et al, dated Mar. 16, 2007, 9 pages.
Supplementary European Search Report for EP 03726447.0, dated Mar. 1, 2006.
International Search Report; International Application No. PCT/US2003/012782, Applicant: Applied Medical Resources Corporation, dated Oct. 28, 2003, 7 pages.
International Search Report; International Application No. PCT/US2006/042336, Applicant: Abdominus, Inc., dated Mar. 14, 2007, 9 pages.
International Search Report; International Application No. PCT/US2010/029865, Applicant: ReShape Medical, Inc., dated Jan. 5, 2011, 9 pages.
Final Office Action; U.S. Appl. No. 11/694,536, dated Mar. 11, 2011, 13 pages.
Final Office Action; U.S. Appl. No. 11/768,152, dated Jan. 19, 2011, 13 pages.
International Search Report; International Application No. PCT/US2011/024082, Applicant: ReShape Medical, Inc., dated Apr. 6, 2011, 10 pages.
International Search Report; International Application No. PCT/US2011/024077; Applicant: ReShape Medical, Inc., dated Apr. 6, 2011, 12 pages.
International Search Report; International Application No. PCT/US2010/042948; Applicant: ReShape Medical, Inc., dated Apr. 1, 2011, 11 pages.
International Search Report; International Application No. PCT/US2010/043136; Applicant: ReShape Medical, Inc., dated Apr. 12, 2011, 9 pages.
International Search Report; International Application No. PCT/US2010/043134; Applicant: ReShape Medical, Inc., dated Apr. 27, 2011, 12 pages.
International Search Report; International Application No. PCT/US2011/0426233; Applicant: ReShape Medical, Inc., dated Apr. 26, 2011, 9 pages.
"ReShape Inflatable Gastric Balloon Going on Trial as Weight Loss Option," MedGadget: Internet Journal of Emerging Medical Technologies. Feb. 4, 2010. (5 pages).
Non-Final Office Action; U.S. Appl. No. 12/723,545; dated Feb. 29, 2012, 10 pages.
Non-Final Office Action; U.S. Appl. No. 12/625,473; dated Jul. 12, 2012; 10 pages.
Non-Final Office Action; U.S. Appl. No. 12/753,751; dated Oct. 5, 2012, 8 pages.
Non-Final Office Action; U.S. Appl. No. 13/074,956; dated Oct. 1, 2012, 8pages.
European Supplementary Search Report; EP Application No. 10802994.3, Applicant: ReShape Medical, Inc., dated Jun. 28, 2013, 8 pgs.

(56) References Cited

OTHER PUBLICATIONS

European Supplementary Search Report; EP Application No. 10802918.2, Applicant: ReShape Medical, Inc., dated Jun. 5, 2013, 6 pgs.
Extended European Search Report; Application No. EP11766679.2, Applicant: Reshape Medical, Inc., dated Dec. 12, 2013, 6 pages.
Non-Final Office Action; U.S. Appl. No. 13/386,650; dated Jun. 3, 2014, 15 pages.
Notice of Allowance; U.S. Appl. No. 12/753,803, dated May 13, 2014, 18 pages.
Extended European Search Report; Application No. EP11740536.5, Applicant: ReShape Medical, Inc., dated Jul. 3, 2014, 8 pages.
Extended European Search Report; Application No. EP11831683.5, Applicant: Reshape Medical, Inc., dated Jul. 3, 2014, 8 pages.
Extended European Search Report; Application No. EP11748141.6, Applicant: Reshape Medical, Inc., dated Feb. 25, 2014, 6 pages.
Final Office Action; U.S. Appl. No. 13/556,032, dated Jan. 28, 2014, 8 pages.
Extended European Search Report; Application No. EP6827098.3, Applicant: Reshape Medical, Corporation, dated Aug. 25, 2014, 3 pages.
Extended European Search Report; application No. EP6847847.8, Applicant: ReShape Medical Corporation, dated Aug. 14, 2014, 5 pages.
Non-Final Office Action; U.S. Appl. No. 13/386,638, dated Jun. 27, 2014, 12 pages.
Canadian 2nd Office Action Application No. CA 2680124, Applicant: Reshape Medical, Inc., dated Jul. 9, 2015, 3 pages.
Canadian Office Action: Application No. CA 2680124, Applicant: Reshape Medical Corporation, dated Nov. 4, 2014, 3 pages.
Canadian Office Action; Application No. CA 2638163, Applicant: Reshape Medical Corporation, dated Mar. 10, 2015, 4 pages.
Canadian Office Action; Application No. CA 2638988, Applicant Reshape Medical Corporation, dated Dec. 22, 2014 3 pages.
Canadian Office Action; Application No. CA 2638988, Applicant Reshape Medical Corporation, dated Mar. 6, 2014, 4 pages.
Canadian Office Action; Application No. CA 2638989, Applicant: Reshape Medical Corporation, dated May 22, 2013 3 pages.
Canadian Office Action; Application No. CA 2638163, Applicant: Reshape Medical, Inc., dated Dec. 8, 2015, 4 pages.
Canadian Office Action; Application No. CA 2640554, Applicant: Reshape Medical Corporation, dated May 27, 2013, 2 pages.
Canadian Office Action; Application No. CA 2691530, dated Dec. 18, 2014, 4 pages.
Canadian Office Action; Application No. CA2484838, Applicant: Reshape Medical, Inc., dated Nov. 13, 2009, 3 pages.
Canadian Office Action; Application No. CA2484838, Applicant: Reshape Medical, Inc., dated Sep. 24, 2010, 3 pages.
Canadian Office Action; Application No. CA2638163, Applicant: Reshape Medical Corporation, dated Jul. 17, 2013, 2 pages.
Canadian Office Action; Application No. CA2638988, Applicant: Reshape Medical Corporation, dated May 28, 2013, 3 pages.
Canadian Office Action; Application No. CA2780085, Applicant: Reshape Medical, Inc., dated Jul. 23, 2012, 2 pages.
European Examination Report; Application No. 03726447.0, Applicant: Applied Medical Resources Corporation: dated Oct. 26, 2007, 4 pages.
European Examination Report; Application No. 08771842.5, dated May 7, 2015, 5 pages.
European Examination Report; Application No. EP06827313.5, Applicant: Reshape Medical Inc., dated Jul. 13, 2015, 4 pages.
European Examination Report; Application No. EP06847847.8, Applicant: Reshape Medical Inc., dated Jul. 13, 2015, 4 pages.
European Examination Report; Application No. EP108002918.2, Applicant: Reshape Medical Inc., dated Dec. 17, 2014, 5 pages.
European Examination Report; Application No. EP108029943, Applicant: Reshape Medical Inc., dated Dec. 18, 2014, 4 pages.
European Supplementary Search Report; Application No. 08771842.5, dated Apr. 24, 2015, 3 pages.
Extended European Search Report; Application EP11740536.5, Applicant: ReShape Medical, Inc., dated Jul. 3, 2014, 8 pages.
Extended European Search Report; Application EP11831683.5, Applicant: Reshape Medical, Inc., dated Jul. 3, 2014, 8 pages.
Extended European Search Report; Application No. 08732989.2, Applicant: Reshape Medical, Inc., dated Oct. 16, 2014, 7 pages.
Extended European Search Report; Application No. EP6827098.3, Applicant: Reshape Medical, Corporation, dated on Aug. 25, 2014, 3 pages.
Extended European Search Report; Application No. EP6827313.5, Applicant: ReShape Medical Corporation, dated Jul. 30, 2014, 5 pages.
Extended European Search Report; Application No. EP6827314.3, Applicant: ReShape Medical Corporation, dated Aug. 1, 2014, 3 pages.
Extended European Search Report; Application No. EP6847847.8, Applicant ReShape Medical Corporation, dated Aug. 7, 2014, 5 pages.
Final Office Action for Japanese Application No. 2014-52972, Applicant: ReShape Medical, Inc., dated Oct. 9, 2015, 8 pages.
Japanese Final Office Action; Application No. JP2013-043712, dated Nov. 15, 2013, 5 pages.
Japanese Office Action; Application No. 2013-142327, dated May 29, 2014, 4 pages.
Japanese Office Action; Application No. 2013-532976; dated Jun. 26, 2015, 10 pages.
Japanese Office Action; Application No. 2014-52972; dated Feb. 25, 2015, 7 pages.
Japanese Office Action; Application No. JP2010-501261, dated Sep. 7, 2012, 10 pages.
Japanese Office Action; Application No. JP2010-515040, dated Jan. 7, 2013, 17 pages.
Japanese Office Action; Application No. JP2012-503759, dated Mar. 24, 2014, 5 pages.
Japanese Office Action; Application No. JP2013-43712, dated Jan. 8, 2015, 8 pages.
Japanese Office Action; Application. No. JP2013-043712, dated Apr. 22, 2013, 5 pages.
Ostrovsky, ReShape Inflatable Gastric Balloon going on Trial as Weight Loss Option; http://www.medgadget.com/2010/02/reshape_inflatable_gastric_bal-loon_system_going_on_trial_as_weight_loss_option.html Feb. 4, 2010, retrieved on 02-10-2-13.
Partial Supplementary European Search Report for European Application No. 11740535.7, Applicant: ReShape Medical, Inc., dated Oct. 20, 2015, 7 pages.
Cronin, Carmel G. et al., "Normal small bowel wall characteristics on MR enterography," European Journal of Radiology 74(2):207-211, Aug. 2010.
Gray, Henry Anatomy of the Human Body. Philadelphia: Lea & Febiger, 1918. Section XI Splanchnology, 2g. The Small Intestine. Bartleby.com, 2000. Web. URL: www.bartleby.com/107/248.html. Accessed: Oct. 26, 2015. 12 pages.
Extended European Search Report; Application No. 16183882.6, Applicant: Reshape Medical Inc., dated Feb. 17, 2017, 9 pages.
European Examination Report; Application No. 11766679.2, Applicant: Reshape Medical Inc., dated Dec. 1, 2016, 4 pages.
European Examination Report; Application No. 11748141.6, Applicant: Reshape Medical Inc., dated Dec. 8, 2016, 3 pages.
Final Office Action for U.S. Appl. No. 14/732,552 dated Aug. 8, 2016, 9 pages.
Final Office Action; U.S. Appl. No. 13/556,032, dated Jan. 28, 2014, 7 pages.
Non-Final Office Action; U.S. Appl. No. 11/263,302; dated Oct. 9, 2012, 6 pages.
Non-Final Office Action; U.S. Appl. No. 13/386,650; dated Jun. 3, 2014, 14 pages.
Notice of Allowance; U.S. Appl. No. 12/753,803, dated May 13, 2014, 9 pages.
Partial Supplementary European Search Report for European Application No. 11740535.7, dated Oct. 20, 2015, 7 pages.
European Search Report for European Application No. 11740535.7, Applicant: ReShape Medical, Inc., dated Mar. 8, 2016, 14 pages.

(56) References Cited

OTHER PUBLICATIONS

Extended European Search Report; Application No. 15198773.2, Application ReShape Medical Corporation, dated Jul. 15, 2016, 7 pages.
Japanese Office Action for Patent Application No. 2015-084207 dated Mar. 16, 2016, 4 pages.
Chou, Chyuan et al., "Structural Effects on the Thermal Properties of PDPS/PDMS Copolymers," Journal of Thermal Analysis, vol. 40, pp. 657-667, 1993.
Extended European Search Report; Application No. 10802993.5, Applicant: Reshape Medical Inc., dated Apr. 19, 2017, 9 pages.
European Search Report; Application No. 06827313.5, Applicant: Reshape Medical Inc., dated Feb. 3, 2017, 5 pages.
Extended European Search Report, Application No. 10759514.2, Applicant: Reshape Medical, Inc., dated Jul. 5, 2017, 10 pages.
Extended European Search Report, Application No. 17162002.4, Applicant: Reshape Medical, Inc., dated Aug. 16, 2017, 10 pages.
Extended European Search Report, Application No. 16153659.4, Applicant: Reshape Medical, Inc., dated Sep. 28, 2016, 7 pages.
European Search Report; Application No. 08732989.2, Applicant: Reshape Medical Inc., dated Sep. 1, 2016, 5 pages.
European Search Report; Application No. 11740536.5, Applicant: Reshape Medical Inc., dated Sep. 1, 2016, 5 pages.
European Search Report; Application No. 15198773.2, Applicant: Reshape Medical Inc., dated Mar. 21, 2017, 4 pages.
Partial Supplementary European Search Report; Application No. 10759514.2, Applicant: Reshape Medical Inc., dated Mar. 27, 2017, 6 pages.

\* cited by examiner

INTRAGASTRIC SPACE FILLER

CROSS-REFERENCE TO RELATED APPLICATION

This application is a continuation of U.S. patent application Ser. No. 11/263,302, filed Oct. 31, 2005, now abandoned which is incorporated herein by reference in its entirety.

FIELD OF THE INVENTION

The present invention is generally related to implantable weight control devices. More particularly, the present invention is related to an intragastric space filler device which is retrievably implantable in a patient.

BACKGROUND OF THE INVENTION

Gastric space fillers used for achieving loss of weight in extremely obese persons have been known in the prior art. All gastric space fillers utilized for this purpose function on the principle that an empty bag or space filler is placed into the stomach through the esophagus. Thereafter, the bag or space filler is filled (fully or partially) with a suitable insufflation fluid, such as saline solution, through a filler tube or catheter which is inserted into the stomach through the mouth or the nose. The space filler occupies space in the stomach thereby leaving less room available for food and creating a feeling of satiety for the obese person. Clinical experience of the prior art has shown that for many obese patients the intragastric space fillers significantly help to control appetite and accomplish weight loss. Among the intragastric bags or space fillers described in the prior art, one type remains connected to a filler tube during the entire time period while the space filler is in the stomach. The tube is introduced into the patient's stomach through the nostrils. Such an intragastric space filler is described, for example, in U.S. Pat. No. 4,133,315.

Garren et al. in U.S. Pat. Nos. 4,416,267 and 4,899,747, entire contents of which are incorporated herein by reference, discloses a stomach insert for treating obesity in humans by reducing the stomach volume comprising a flexible torus-shaped inflatable space filler having a central opening extending therethrough. At least a portion of the space filler has a self-sealing substance to facilitate puncture thereof with a needle for inflating the space filler and sealing off the puncture upon removal of the needle. The method herein comprises positioning the space filler inside the stomach of the person being treated for obesity so as to reduce the stomach volume. The Garren et al. stomach insert works satisfactorily to control the appetite. However, the insert may deflate and collapse unexpectedly resulting in obstructing the pylorus or small intestines. It appears desirable to have a space filler system that yields some noticeable warning and prompts timely removal of the implant from the patient.

Several surgical techniques have been tried which bypass the absorptive surface of the small intestine or aim at reducing the stomach size by either partition or bypass. These procedures have been proven both hazardous to perform in morbidly obese patients and have been fraught with numerous life-threatening postoperative complications. Moreover, such operative procedures are often difficult to reverse.

Non-surgical approaches for the treatment of obesity include voluntary dieting which is often unsuccessful since most persons do not possess sufficient willpower to limit the intake of food. Other approaches include the use of stomach fillers such as methylcellulose, often taken in the form of tablets. The methylcellulose expands in the stomach leaving the person with a filled-up feeling. Also, inflatable bag and tube combinations have been proposed wherein the bag is swallowed into the stomach and the tube attached thereto is used to periodically inflate the bag, particularly just prior to mealtime or during the meal. Once the person has eaten, the bag can be deflated all at once, or it can be deflated gradually over a period of a few hours so as to simulate the condition of digestion occurring and the gradual reduction of stomach contents.

U.S. Pat. No. 4,133,315 issued on Jan. 9, 1979, entire contents of which are incorporated herein by reference, discloses such an inflatable bag and tube combination. The tubing remains attached to the bag and inside the esophagus of the person being treated. These tubes are often the cause of erosions and ulcerations of the esophagus. This patent also discloses a gastrotomy method wherein the permanently attached tube used to distend the stomach bag extends through an opening in the stomach wall as well as an opening in the abdomen.

U.S. Pat. No. 4,246,893 issued on Jan. 27, 1981, entire contents of which are incorporated herein by reference, discloses an inflatable bag and tube combination which is surgically positioned outside and adjacent to the stomach. Upon inflation of the bag, the upper abdomen is distended and the stomach compressed to thereby produce a sense of satiety which reduces the person's desire to ingest food.

U.S. Pat. No. 4,598,699 issued on Jul. 8, 1996, entire contents of which are incorporated herein by reference, discloses an endoscopic instrument for removing an inflated insert from the stomach cavity of a person being treated for obesity comprising an elongated flexible tube having passageways therein and a holding device at the distal end of the flexible tube that is constructed and arranged to grasp and stabilize the inflated stomach insert.

Certain prior art discloses a gastric stimulator apparatus for stimulating neuromuscular tissue in the stomach, for example, U.S. Pat. No. 6,826,428. In one disclosure, it provides a method of regulating gastrointestinal action using a stimulatory electrode and a sensor to provide retrograde feedback control of electrical stimulation to the GI tract or to the stomach.

U.S. Pat. No. 4,694,827 issued on Sep. 22, 1987, entire contents of which are incorporated herein by reference, discloses a balloon insertable and inflatable in the stomach to deter ingestion of food and having, when inflated, a plurality of smooth-surfaced convex protrusions disposed to permit engagement of the stomach wall by the balloon only at spaced localities, for minimizing mechanical trauma of the stomach wall by the balloon.

U.S. Pat. No. 6,746,460 issued on Jun. 8, 2004, entire contents of which are incorporated herein by reference, discloses an expandable device that is inserted into the stomach of the patient that is maintained within by anchoring or otherwise fixing the expandable device to the stomach walls. Such expandable devices have tethering regions for attachment to the one or more fasteners which can be configured to extend at least partially through one or several folds of the patient's stomach wall. Such fasteners can be formed in a variety of configurations, e.g., helical, elongate, ring, clamp, and they can be configured to be non-piercing.

Hence, reducing the size of the gastric compartment has been shown to induce weight loss in a significant percentage of people, and the present invention is aimed at a device which non-operatively reduces the size of the gastric compartment and which is easily removed. One aspect of the invention discloses a gastric space filler device with programmed volume-adjustable capability or warning signals for device potential failure.

SUMMARY OF THE INVENTION

In accordance with preferred embodiments of the present invention, some aspects of the invention relate to a gastric space filler system for treating obesity in a patient by reducing the stomach volume comprising at least two flexible inflatable space fillers secured to each other, a first space filler being inflatable to a volume inside the stomach and not in fluid communication with the other remaining space fillers, wherein at least a portion of the first space filler is made of a biodegradable material. In one embodiment, the gastric space filler device of the present invention is characterized with little or minimal effects of bowel obstruction, erosion, perforation and infection to a patient. In one preferred embodiment, the space filler generally approximates the shape of the stomach and accomplishes more complete space filling (up to 95% of stomach volume).

In one embodiment, the space filler system comprises pressure reading means for transmitting internal pressure readings of one space filler to a receiver or controller. In a further embodiment, a pressure sensor element is mounted on a first of the at least two space fillers of the gastric space filler system for sensing an internal pressure of the first space filler. In a further embodiment, the pressure sensor element further comprises a transmitter for wirelessly transmitting the measured internal pressure signal to a receiver outside a body of the patient. The measured internal pressure is compared to a pre-determined threshold pressure for signaling removal of the filler system. In some embodiment, the pressure sensor element may be substituted by a pH sensor, a flow-rate sensor, a temperature sensor, an electrolyte sensor, or the like.

In some embodiment, two of the at least two space fillers of the gastric space filler system are configured to be in tandem inside the stomach pouch or are configured to be substantially parallel to each other.

In one embodiment, at least one of the two space fillers of the gastric space filler system is anchored to an inner wall of the stomach. In a further embodiment, the anchoring action is arranged and configured to activate the anchoring mechanism when the space filler is inflated while contacting the inner wall of the stomach, and to reverse the anchoring mechanism when the filler is deflated.

In a further embodiment, at least a portion of the at least two space fillers is ultrasonically visible. One method of visualization is to have ultrasonically visible air bubble at or on part of the space filler. Another method is to incorporate ultrasonically visible contrast agent at or on part of the space filler.

In one embodiment, the gastric space filler device is configured to be deliverable through an esophagus of the patient. In another embodiment, at least a portion of an external surface of the space filler is treated with an anti-acid substance, corrosion-resistant substance or anti-adhesion substance, wherein the substance comprises polytetrafluoroethylene, inert material, or other biological material (such as albumin, melatonin, phosphorylcholine, or protein) that are biocompatible. Methods of treating the surface include coating, painting, dipping, impregnation, and the like.

Some aspects of the invention provide a gastric space filler device for treating obesity in a patient by reducing the stomach volume comprising an inflatable space filler and a safety element secured to the space filler, wherein the safety element comprises a mechanism to yield a noticeable signal for causing a removal of the space filler.

Some aspects of the invention provide a gastric space filler device for treating obesity in a patient by reducing a stomach volume comprising an inflatable space filler with a first reference shape at an inflated state and means for substantially maintaining the first reference shape at a deflated state. In one embodiment, the means for substantially maintaining the first reference shape at the deflated state is to provide a spiral supportive ridgeline onto the space filler, wherein the spiral ridgeline may comprise a material similar to material of the space filler. In another embodiment, the means for substantially maintaining the first reference shape at the deflated state is to provide a plurality of cross bars inside an interior space of the space filler.

Some aspects of the invention provide a gastric space filler device for treating obesity in a patient by reducing a stomach volume comprising an inflatable space filler with a first cross-sectional circumference dimension at an inflated state and means for maintaining a second cross-sectional circumference dimension with at least 75 percentage of the first circumference dimension at a deflated state.

In one embodiment, any of the at least two space fillers of the gastric space filler system has a central opening extending therethrough. In another embodiment, one of the at least two space fillers is fabricated from polyurethane sheet material. In still another embodiment, the polyurethane sheet material comprises a single layer. Other polymer sheet material, compliant (for example, silicone or Nylon) or non-compliant (for example, polyethylene or polytetrafluoroethylene), may also be suitable for the intended purposes.

In one embodiment, the biodegradable material for the gastric space filler system is selected from a group consisting of polymers or copolymers of lactide, glycolide, caprolactone, polydioxanone, trimethylene carbonate, polyorthoesters and polyethylene oxide. In another embodiment, one of the at least two space fillers is made of a non-biodegradable material selected from a group consisting of polyester, polypropylene, Nylon, polyethylene, co-polymers thereof, and the like.

Some aspects of the invention relate to a method of treating obesity in a patient comprising the steps of: providing a deflated gastric space filler system with an infusing tube releasably attached thereto inside an elongate catheter sheath, wherein the space filler system comprises at least two flexible inflatable space fillers secured to each other, a first space filler being inflatable to a volume inside the stomach and not in fluid communication with the remaining space fillers, wherein at least a portion of the first space filler is made of a biodegradable material; introducing the catheter sheath through the mouth and into the stomach; urging the gastric space filler system out of the catheter sheath and into the stomach; inflating each space filler through the infusing tube with a given amount of fluid to increase the volume thereof; and removing the infusing tube from the stomach and out through the mouth.

In one embodiment, the inflating step comprises inflating at least one of the space fillers to a pressure slightly higher than a stomach pressure of the patient, preferably to a pressure difference of at least 1 mm Hg above a stomach pressure of the patient. In one embodiment, the method further includes a step of detecting a deflated space filler that triggers the step of removing the gastric space filler device.

In one embodiment, the method for removing the gastric space filler system from the stomach is by introducing extraction means through the mouth and into the stomach, grasping and puncturing all of the at least two space fillers with the extraction means, and then withdrawing the deflated gastric space filler out of the stomach and through the mouth. In one embodiment, the extraction means includes a fiberoptic gastroscope with needle biopsy forceps.

In one embodiment, the method for removing the gastric space filler system from the stomach is by radially shrinking all of the at least two space fillers to fit inside a lumen of the extraction catheter sheath, and then withdrawing the deflated gastric space filler system out of the stomach and through the mouth.

In a further embodiment, the method further includes a step of detecting an internal pressure of at least one space filler prior to the step of removing the gastric space filler device.

Some aspects of the invention provide a method of treating obesity in a patient comprising the steps of: providing an inflatable gastric space filler device, wherein the device comprises a first space filler and a second space filler enclosed within the first space filler, the device comprising a safety mechanism to yield a noticeable signal for causing a removal of the device; introducing the device through the mouth and into the stomach; and removing the device once the noticeable signal is received.

Some aspects of the invention provide a method of treating obesity in a patient with minimal nausea effects comprising implanting a stomach space filler device coated with an anti-nausea agent.

Some aspects of the invention provide a method of treating obesity in a patient comprising the steps of a) providing a deflated gastric space filler device with an infusing tube releasably attached thereto inside an elongate catheter sheath, wherein the space filler device comprises an inflatable space filler and a safety mechanism secured to the space filler, wherein the safety mechanism yields a noticeable signal for causing a removal of the space filler; b) introducing the catheter sheath through the mouth and into the stomach; c) urging the gastric space filler device out of the catheter sheath and into the stomach; d) inflating the space filler through the infusing tube with a given amount of fluid to increase the volume thereof; and e) removing the infusing tube from the stomach and out through the mouth.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

The preferred embodiments of the present invention described below relate particularly to an intragastric space filler device comprising at least one space filler for reducing the stomach volume and one space filler made of biodegradable material, wherein the biodegradable space filler (that is, at least a portion of the space filler is made of biodegradable material) is used as a warning signal for timely removal of the space filler device. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

The stomach has a lot of functions and one of these is to expand and contract. This J-shaped organ has very active muscles. These muscles expand and contract depending on how much food is in the stomach. This contraction is a form of mechanical breakdown of the food. The purpose of this breakdown is to increase the available surface area for the chemicals to act on it. The gastric glands of the stomach secrete enzymes that perform chemical breakdown, partly digesting the proteins. Pepsin is the enzyme that breakdowns protein. The gastric gland also secretes hydrochloric acid that kills almost all the bacteria in the food. It also secretes mucus that protects the stomach wall from the hydrochloric acid. By the time all the food is mechanically and chemically broken down, the food becomes a semi-fluid substance that leaves the stomach by peristalsis entering the small intestine.

The structure of the stomach is quite unique. It can be divided into four subdivisions: the cardia, the fundus, the body, and the pylorus. The cardia is the region that is closest to the heart and is where the esophagus is connected to the stomach. The fundus is the region that curves above the rest of the stomach (with respects to a person who is standing upward). The body of the stomach is the largest region located in the center. The pylorus is the region that is connected to the small intestine. The cardia and the pylorus have sphincter muscles that regulate the movement of food and fluids. The hydrochloric acid normally does not go back up the esophagus. When one vomits and has a burning sensation in the esophagus, it is the hydrochloric acid from the stomach.

The volume of the human stomach varies depending on the person. Generally, human stomachs have a volume about one liter. Since the stomach has the ability to expand, it can hold much more food. The human stomach can be distended up to four liters, which is more than one gallon. Imagine your stomach to be an empty one-gallon milk carton. There is plenty room for food.

Double Space Filler System

Figure 1:
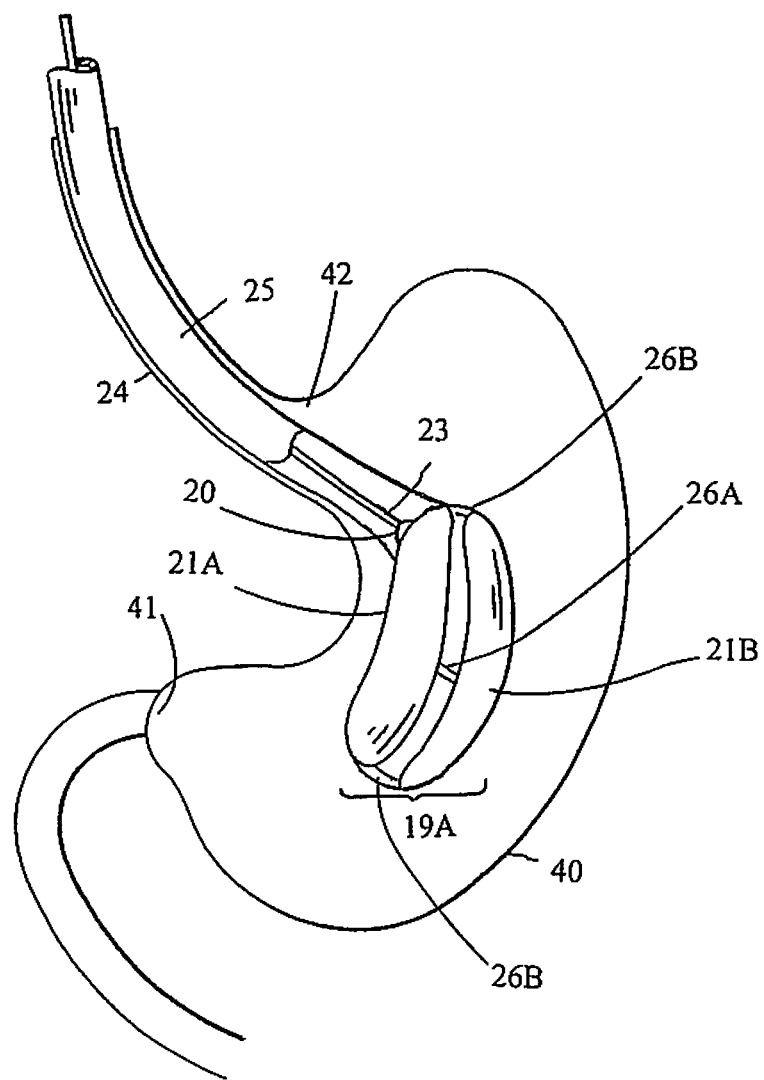
FIG. 1 shows a gastric space filler system with two space fillers secured to and in parallel to each other.

FIGS. 1-14 show one or alternate embodiment of a gastric space filler device and delivery means for implanting and retrieving the gastric space filler device of the present invention. FIG. 1 shows a stomach bubble or space filler system 19A with two space fillers 21A, 21B secured to and in parallel to each other, whereas FIG. 3 shows a gastric space filler system 19B with two space fillers 22A, 22B secured to and in tandem to each other. Both space fillers of the gastric space filler system are deflated, collapsed and retracted within a catheter sheath 25 during the delivery phase or the retrieval phase of the device.

In a preferred embodiment, the gastric space filler system comprises two space fillers, wherein the second space filler is enclosed within the first space filler, wherein at least a portion of the first space filler is made of a biodegradable material and/or with a pressure sensor element for measuring the pressure of the first space filler. In a further embodiment, the gastric space filler system comprises two space fillers, wherein the second space filler is enclosed within the first space filler, wherein at least a portion of the first space filler is made of a biodegradable material and with a sensor element for measuring the property of the content of the first space filler, wherein the property includes pH, temperature, electrolyte type, electrolyte concentration, and the like. In another embodiment, the space between the first space filler and the second space filler is filled with a fluid or saline plus a dye or odor for earlier detection, when the first space filler is compromised, deflated, or leaked.

In one embodiment, the inner surface and/or the outer surface of the delivery catheter sheath is treated to be hydrophilic or to have reduced surface friction. The space filler system 19A has a sealed inlet 20 that allows fluid or saline to be infused into the space fillers via an infusing tubing 23 or a needle with an infusing tubing which is connected to an external fluid source. In one embodiment, the sealed inlet has a self-scaling substance to facilitate puncture thereof with a needle for inflating the space filler and sealing off the puncture upon removal of the needle. In another embodiment, the sealed inlet is equipped with a one-way check valve for receiving infusing fluid or saline.

The catheter sheath 25 or delivery device for the gastric space filler system passes through the esophagus 24 and cardiac notch 42 into the stomach 40 of a patient. Once it is delivered to the stomach, the space fillers are inflated. In one embodiment, at least one of the space fillers is a non-compliant one that is inflated to a pressure slightly higher than the local atmospheric pressure or stomach pressure, preferably a pressure difference of about 1-20 mm Hg, more preferably about 1-5 mm Hg. One rationale of a higher pressure for the space filler is to maintain the desired occupied space volume, though the internal pressure might drift a fraction of the mm Hg pressure over the course of implantation. In some aspects of the invention, the gastric space filler device 19A comprises a plurality of connecting members 26A, 26B between the second space filler 21B and the first space filler 21A that is connected to the infusing tubing 23 via the sealed inlet.

In one embodiment, the connecting members are made of flexible and/or elastic material. In another embodiment, the connecting members are made of solid material that allows no fluid communication between the two space fillers. In one embodiment, a plunger is used to push the space filler device out of the lumen of the delivery device. In an alternate embodiment, the plunger of the delivery means comprises a forward-pulling mechanism at the very distal end distal to the space filler device. During the delivery phase, the space filler device is under axial tension (i.e., under some pulling force between the distal end and the proximal end of the flexible space filler) to cause minimal circumferential profile for easy insertion into the sheath.

Figure 2:
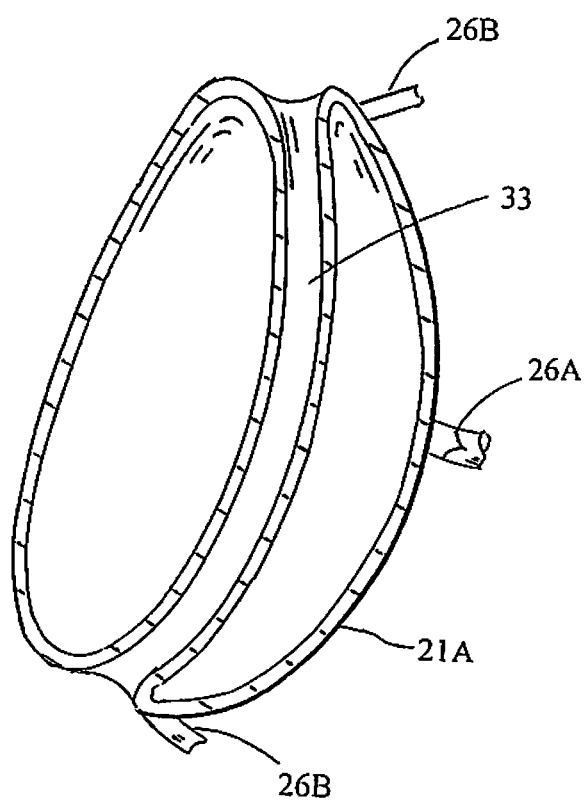
FIG. 2 shows a first space filler of the two space fillers in FIG. 1 with a central passageway therethrough.
Figure 3:
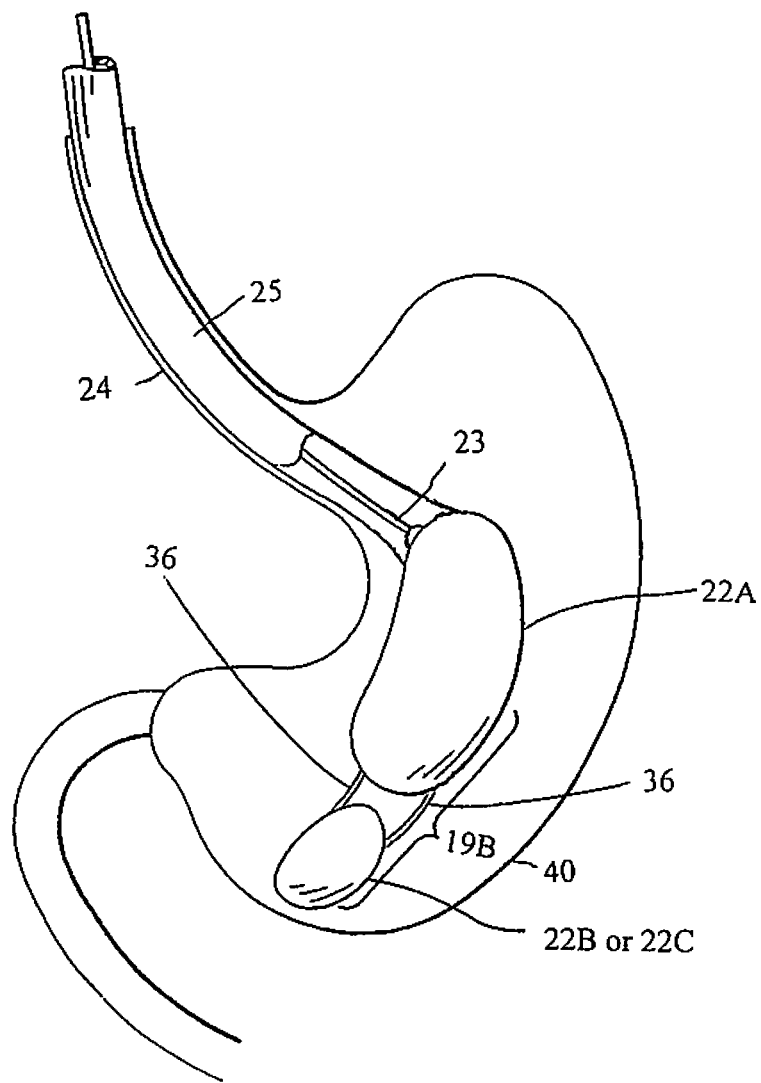
FIG. 3 shows a gastric space filler system with two space fillers secured to and in tandem to each other.

FIG. 2 shows a first space filler 21A of the two space fillers in FIG. 1 with a central passageway 33 therethrough. In one embodiment, the gastric space filler comprises a plurality of passageways therethrough, wherein some passageways are connected to one another. In one embodiment, at least one connecting member 26A comprises a one-way check valve or seal enabling the fluid to flow from the first space filler 21A into the second space filler 21B, but preventing fluid from returning back to the first space filler 21A. In some aspects of the invention as shown in FIG. 3, the gastric space filler device 19B comprises a plurality of connecting members 36 between the second space filler 22B and the first space filler 22A, wherein the first space filler is connected to the infusing tubing via the sealed inlet.

Some aspects of the invention provide a gastric space filler system for treating obesity in a patient by reducing the stomach volume comprising at least two flexible inflatable space fillers secured to each other, each space filler being inflatable to a volume inside the stomach and a first space filler 21A is in one-way fluid communication with the remaining other space fillers 21B, wherein at least a portion of the first space filler 21A is made of a biodegradable material. In one embodiment, a check valve permits the flow of fluid in only one direction from the first biodegradable space filler through a conduit to the second space filler.

In one embodiment, the biodegradable portion of the biodegradable space filler is sized and configured to biodegrade at a specified time duration, the biodegradation of the biodegradable space filler and its subsequent deflation serving as a warning signal for retrieving the whole gastric space filler device. There provides a safety feature when the pressure sensor on the biodegradable space filler emits a low-pressure signal as a result of space filler deflation. Some aspects of the invention provide a warning window (that is, a time period) to remove or retrieve the gastric space filler system when one space filler is deflated or signaled with low pressure. This would prevent the catastrophic or life-threatening blocking/obstructing of the pylorus 42 by a completely (all space fillers in this case) deflated space filler system. In one embodiment, the gastric space filler device might be retrieved at a predetermined post-implantation time, for example at 6 months post-implantation.

Figure 4:
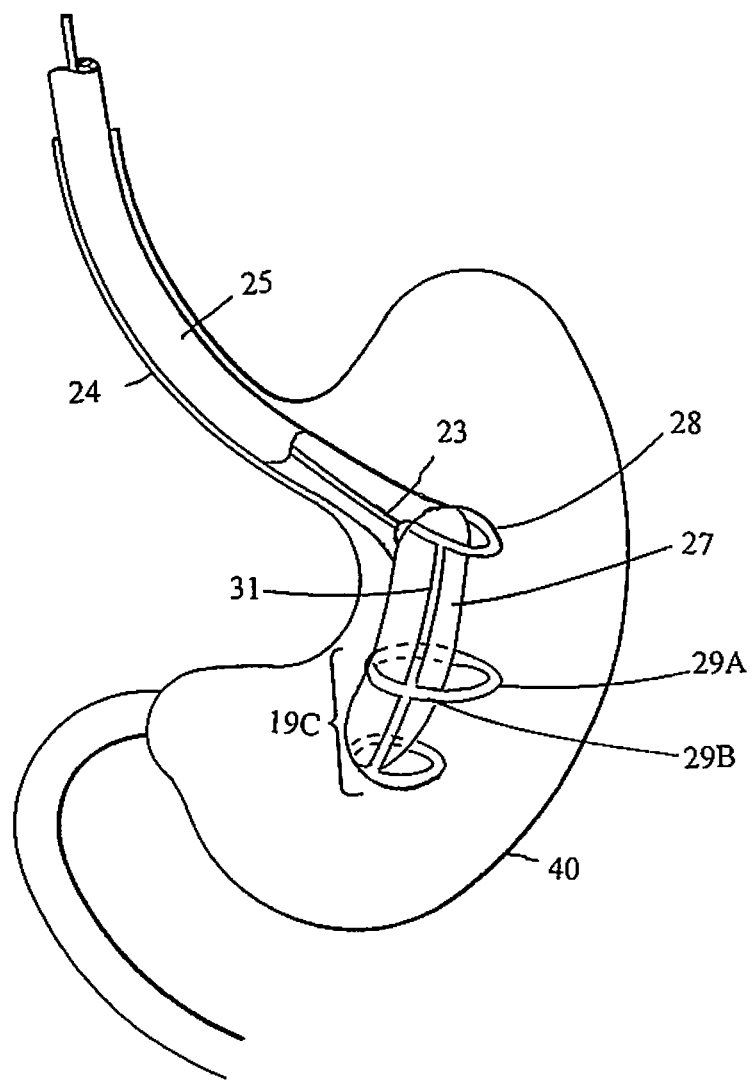
FIG. 4 shows a gastric space filler system having an inflatable space filler with a support mechanism thereto.

FIG. 4 shows a gastric space filler system 19C with an inflatable space filler 27 and a plurality of radially expanded support elements 28 thereon, wherein each support element comprises a space filler contact portion 29B and a suspended non-space filler contact portion 29A. The radially expanded support elements may be secured to each other via a crossing bar 31 or other connecting mechanisms. In one embodiment, the radially expanded support element is sized and configured to stabilize the space filler inside the stomach by distension against the stomach wall.

Figure 5:
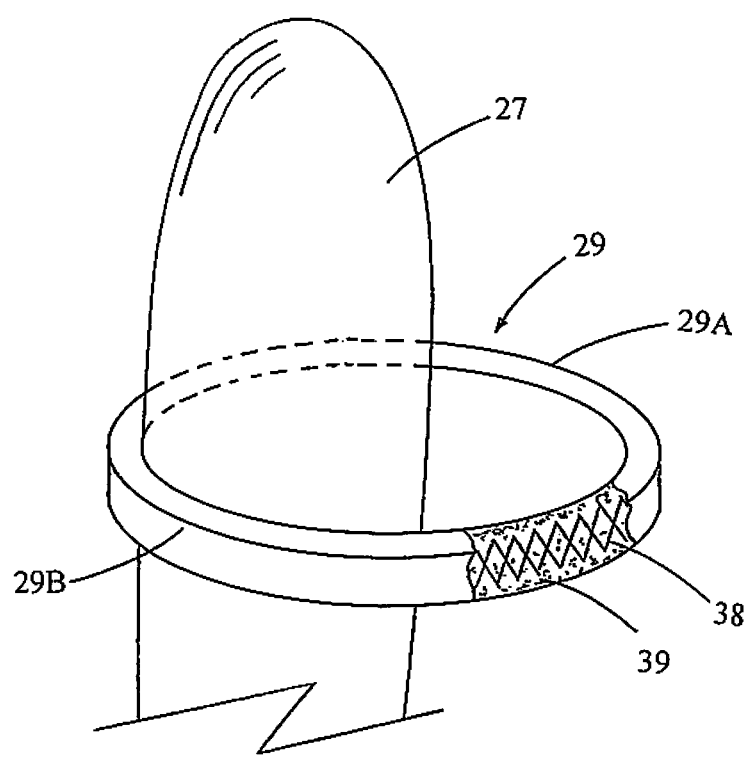
FIG. 5 shows a cross-sectional view of the support mechanism of FIG. 4.

FIG. 5 shows a cross-sectional view of one support element of FIG. 4. In one embodiment, the support element 29 comprises a meshed stenting structure 38 wrapped or enclosed with biocompatible elastomeric material 39, such as silicone, polyurethane, latex, and the like. In one embodiment, the elastomeric material comprises a high percentage of voids or micropores, like a sponge or foam. In one embodiment, the meshed stenting structure is similar to a cardiovascular stent that is either self-expandable or balloon expandable. In one embodiment, the meshed stenting structure is mechanically crimpable or may be made of temperature sensitive shape memory Nitinol.

Figure 11:
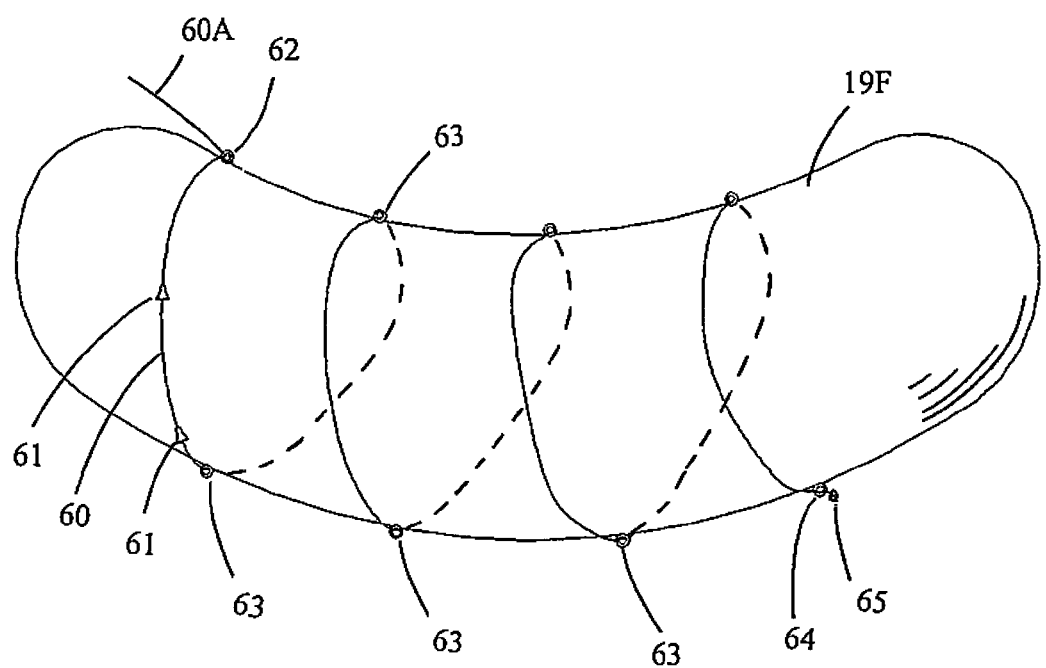
FIG. 11 shows one embodiment of an adjustable space filler system.

One mechanism of mechanically crimping the meshed stenting structure is illustrated in FIG. 11. In a first step of operations, the support element is arranged and configured to be crimped circumferentially or radially inwardly to a smaller profile, together with the deflated space filler, configured to be retracted into the delivery catheter sheath. In a second step of operations, the support element self-expands after releasing the constraint thereon from the catheter sheath, along with the inflated space filler, to occupy an appropriate space inside the stomach 40. In a third step of operations during the retrieval phase, a retriever instrument with certain crimping capability is advanced into the stomach to orient the support element and to crimp the element to a small profile configured to be retracted within the lumen of the retriever instrument (for example, a retrieving catheter sheath). The deflated space filler, and together with the crimped supporting elements, are withdrawn from the stomach to outside the body of the patient.

Figure 8:
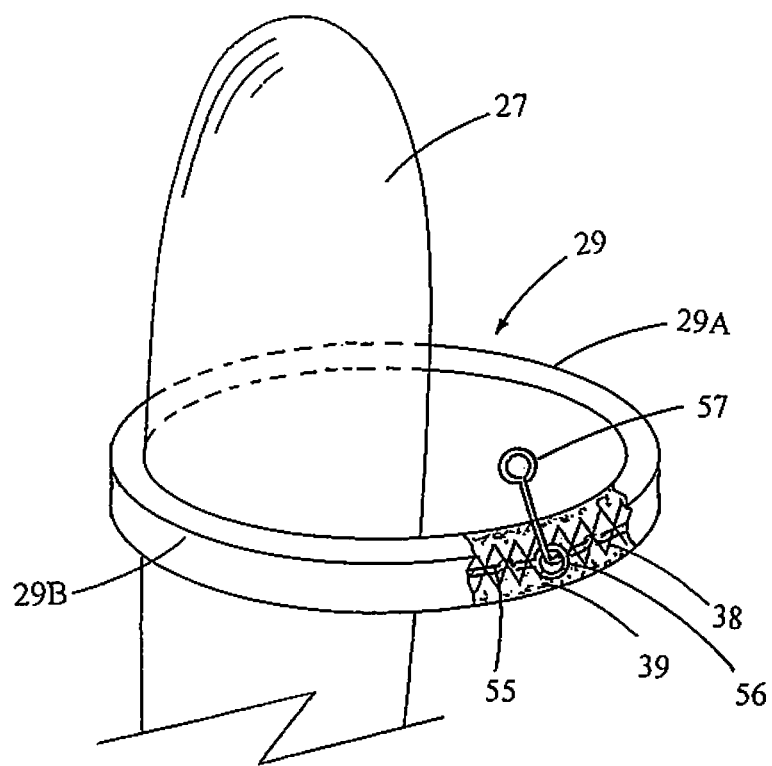
FIG. 8 shows one embodiment of removing a gastric space filler system from the patient.

At about the middle section of the meshed stenting device 38 circumferentially, there provide some crossing points of any two mesh struts. As illustrated in FIG. 8, a tether 55 extends through a front side and a backside of each crossing point alternately. The tether is then joined in a loop with one end of the tether extending through a loop 56 in the other end of the tether and extending slightly out of the plane with an end loop 57. At a retrieval time, the end loop 57 is snatched or grasped by a retriever apparatus (such as the apparatus having a hook, a grasper, or the like) and pulled toward outside of the mouth, enabling collapsing circumferentially the stenting structure to a much smaller profile for removal out of the body.

The device of the present invention intends to provide mechanisms for preventing or avoiding migration, bowel obstruction, bleeding diathesis, erosion, perforation of stomach or any internal organs, and the like. Some complications are acceptable if the benefits of device design far outweigh the risks, such as access site related minor complications, some patient discomfort due to the presence of the device or due to access site related issues, nausea, feeling of bloating, and the like.

U.S. Pat. No. 6,890,300, entire contents of which are incorporated herein by reference, discloses a MEMS (microelectrical mechanical systems) chip sensor based upon detection of an induced inductance in the sensor. The sensor is used in an environment for detection of fluid pressure. The method and system is particularly useful in humans to sense pressure changes.

U.S. Pat. No. 6,939,299, entire contents of which are incorporated herein by reference, discloses an implantable miniaturized pressure sensor integrates a capacitor and an inductor in one small chip, wherein the capacitor has an upper capacitor plate and a lower capacitor plate connected to one or more spiral inductor coils. The sensor is micromachined from silicon to form a thin and robust membrane disposed on top of the upper capacitor plate to sense an external fluid pressure. The resonant frequency of the sensor can be remotely monitored and continuously measured with an external detector pick up coil disposed proximate the sensor.

Some aspects of the invention provides a method for determining fluid pressure within a patient or within a space filler comprising: (a) providing a wireless capacitive MEMS chip sensor comprising an inductance coil and spaced apart capacitor plates as an inductive-capacitive circuit, with the fluid in pressure contact with one of the capacitive plates; (b) inducing a mutual inductance as an external signal into the sensor to produce the resonant frequency response as an internal signal from the sensor; and (c) determining the fluid pressure within the patient externally of the patient from the internal signal as a function of the resonant frequency response from the sensor resulting from a change in capacitance of the sensor due to a variation in the spacing of the plates produced by the fluid pressure of the fluid from the sensor resulting from the change in the series resistance. A pressure sensor element and methods of use are well known to one skilled in the art, for example the MEMS unit disclosed in U.S. Pat. No. 6,890,300 or U.S. Pat. No. 6,939,299.

Space Filler with Safety Features

Figure 6:
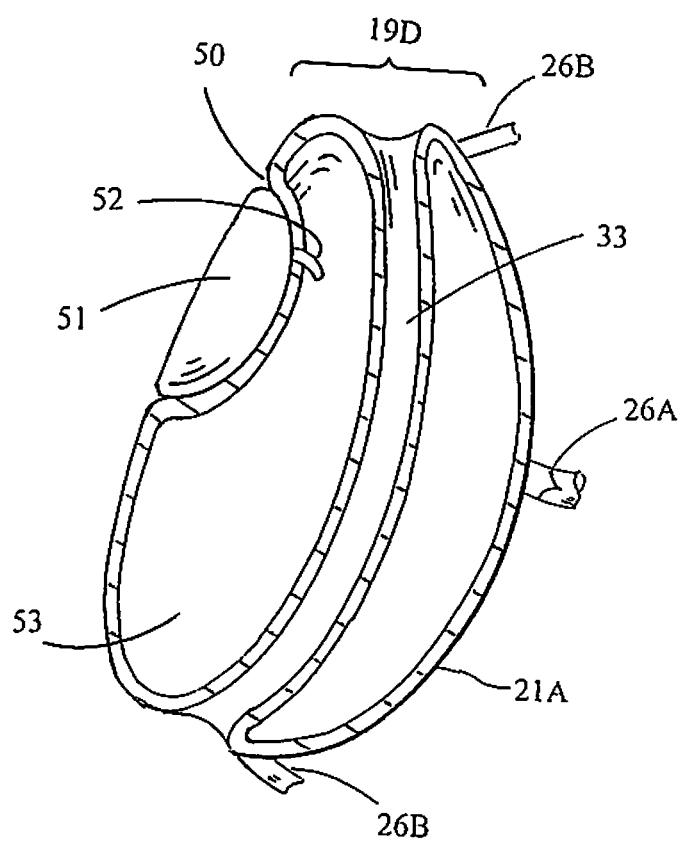
FIG. 6 shows a pressure sensor element mounted on a space filler in accordance with the principles of the present invention.

FIG. 6 shows a pressure sensor element 51 (which may be similar to the one disclosed in U.S. Pat. No. 6,890,300) mounted on a space filler 21A in accordance with the principles of the present invention. In one embodiment, a gastric space filler device 19D comprises a recess area 50 sized and configured to appropriately receive and mount a pressure sensor element 51. The sensor element 51 comprises an opening 52 in pressure communication with an internal void 53 of the space filler device 19D.

Some aspects of the invention provide a pressure sensor element to be mounted on a first of the at least two space fillers of the gastric space filler system for sensing an internal pressure of the first space filler. In one embodiment, the pressure sensor element is mounted on the biodegradable space filler of the gastric space filler system. In another embodiment, a pressure sensor element is mounted on any or all of the at least two space fillers of the present invention. In a further embodiment, the pressure sensor element further comprises a transmitter for wirelessly transmitting the measured internal pressure to a receiver outside a body of the patient or recipient.

Figure 7:
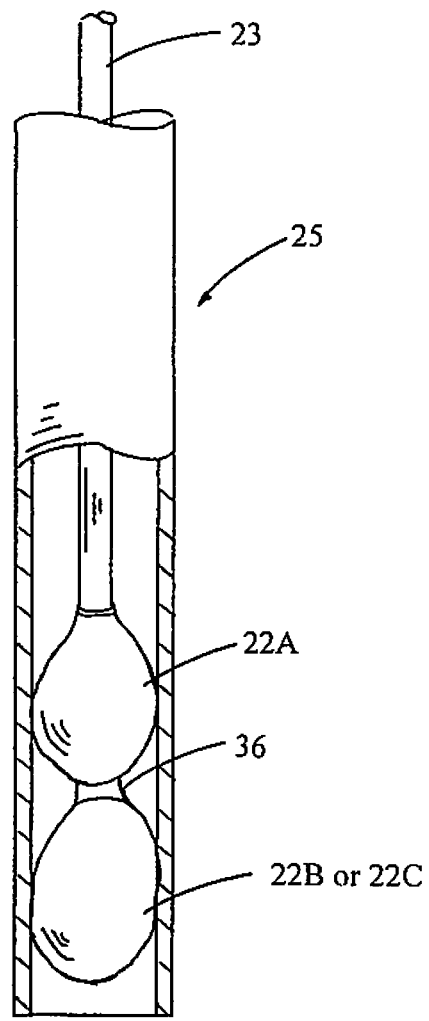
FIG. 7 shows a delivery apparatus for non-surgically implanting a gastric space filler system.

FIG. 7 shows a standard catheter sheath for deploying a gastric space filler device to a patient, wherein the gastric space filler device comprises at least two space fillers 22A and 22B connected by means of connecting members 36. In one embodiment, after advancing the catheter sheath into about the stomach, the infusing tubing 23 serves as a pushing plunger for pushing the gastric space filler device into the stomach of the patient. Thereafter, the space fillers are filled with saline or fluid via the infusing tubing from an external fluid/saline source. Some aspects of the invention provide a method of treating obesity in a patient comprising the steps of: (A) providing an inflatable gastric space filler system with an infusing tube releasably attached thereto inside an elongate catheter sheath, wherein the space filler system comprises at least two flexible inflatable space fillers secured to each other, a first space filler being inflatable to a volume inside the stomach and not in fluid communication with the remaining one or other space fillers, wherein at least a portion of the first space filler is made of a biodegradable material; (B) introducing the catheter sheath through the mouth and into the stomach; (C) urging the gastric space filler system out of the catheter sheath and into the stomach; (D) inflating each space filler through the infusing tube with a given amount of fluid to increase the volume thereof; and (E) removing the infusing tube from the stomach and out through the mouth.

In one embodiment as illustrated in FIG. 2, a gastric space filler device 19B for treating obesity in a patient by reducing the stomach volume comprising a flexible inflatable space filler 22A and a safety element 22C secured to the space filler 22A, wherein the safety element yields a noticeable signal for causing removal of the space filler device. In one embodiment, the safety element is a visible dye so that, when the space filler is compromised, visible dye appears in urine shortly. In one embodiment, the safety element is a special odor so that, when the space filler is compromised or leaked, smellable odor appears in urine shortly. In a further embodiment, the safety element comprises biodegradable material so that when the safety element biodegrades prematurely, it yields a signal for prompt removal, such as the decomposed/biodegraded pieces.

The safety element may comprise means for maintaining "appropriate shape retention" of the space filler so the compromised space filler (either via leaking or collapsing) does not cause bowel obstruction. The "appropriate shape retention" is herein to mean that the residual cross-sectional shape or circumference dimension after filler compromise maintains a value not to cause bowel obstruction. In one embodiment, the appropriate dimension retention is at least 50%, preferably 75%, of the pre-compromised reference value.

Some aspects of the invention provide a gastric space filler device for treating obesity in a patient by reducing the stomach volume comprising an inflatable space filler with a reference shape and means for substantially maintaining the reference shape after the space filler is deflated by accident or intentionally. For illustration purposes, the means for maintaining the reference shape of the space filler is to incorporate a relatively rigid supportive spiral ridgeline along the interior surface of the space filler. By way of illustration, the supportive ridgeline is similar to the reinforcing spiral elements along an internal surface of a hose. The ridgeline is sized (at least one complete hoop circle) and configured to resist compressive pressure from the stomach wall, but is flexible and collapsible by a retrievable instrument either through clamping, crimping or other mechanical destructive methods. In one embodiment, the ridgeline is made of the same biocompatible material as the space filler. In another embodiment, the ridgeline is an integral part of the space filler. In still another embodiment, the ridgeline contains a wholly enclosed elastic metal wire or coil by the same biocompatible material of the space filler.

For further illustration purposes, the means for maintaining the reference shape of the space filler is to incorporate a plurality of relatively rigid cross bars inside the interior space of the space filler, wherein each end of the cross bars is secured to the interior wall of the space filler. The structure of the cross bars is sized and configured to resist compressive pressure from the stomach wall, but is flexible and collapsible by a retrievable instrument either through clamping, crimping or other mechanical destructive methods. In one embodiment, the cross bar is made of the same biocompatible material as the space filler. For further illustration purposes, the means for maintaining the reference shape of the space filler is to incorporate a foam material inside the interior volume of the space filler. The structure of the foam material is sized and shaped to resist compressive pressure from the stomach wall, but is flexible and collapsible by a retrievable instrument either through clamping, crimping, drawing string technique (as shown in FIG. 11) or other mechanical methods. By maintaining the shape of the space filler substantially similar to the reference shape after the space filler is deflated by accident or intentionally would cause the space filler remain inside the stomach and not to obstruct the bowel.

Figure 13:
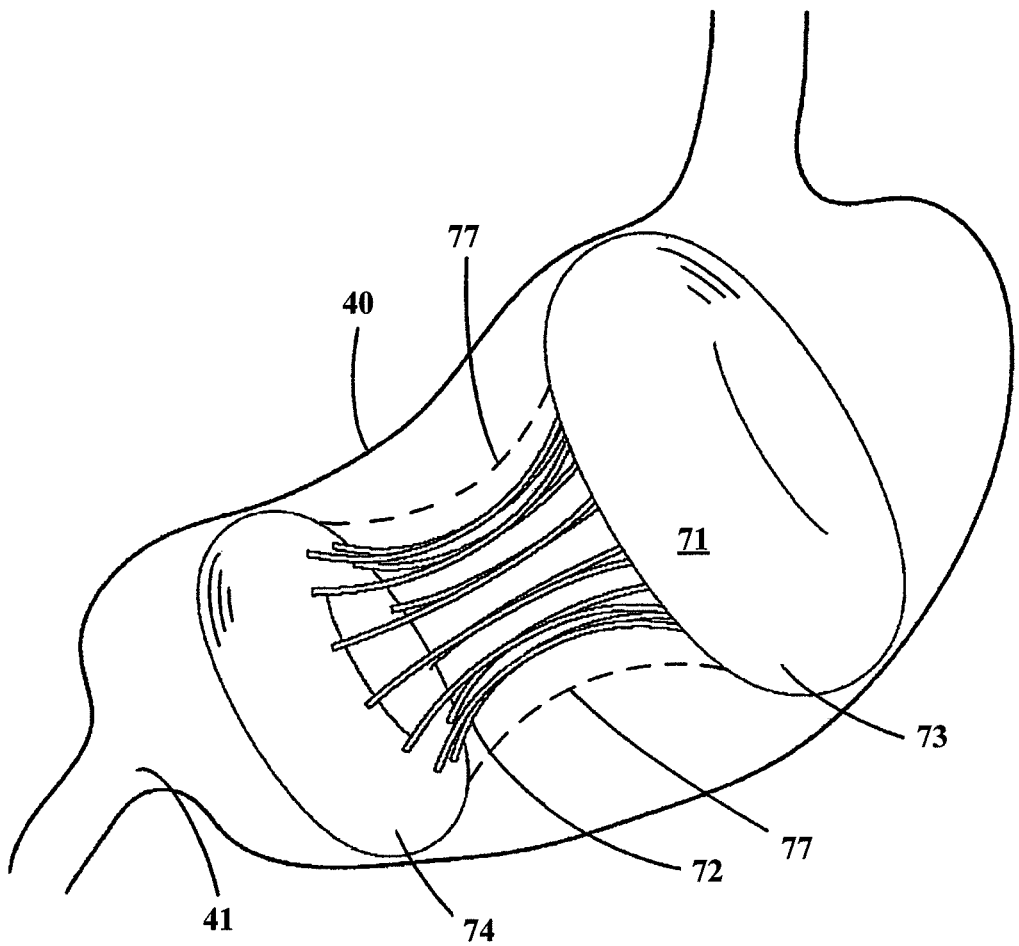
FIG. 13 shows a space filler device comprising a shape retention mechanism.
Figure 14:
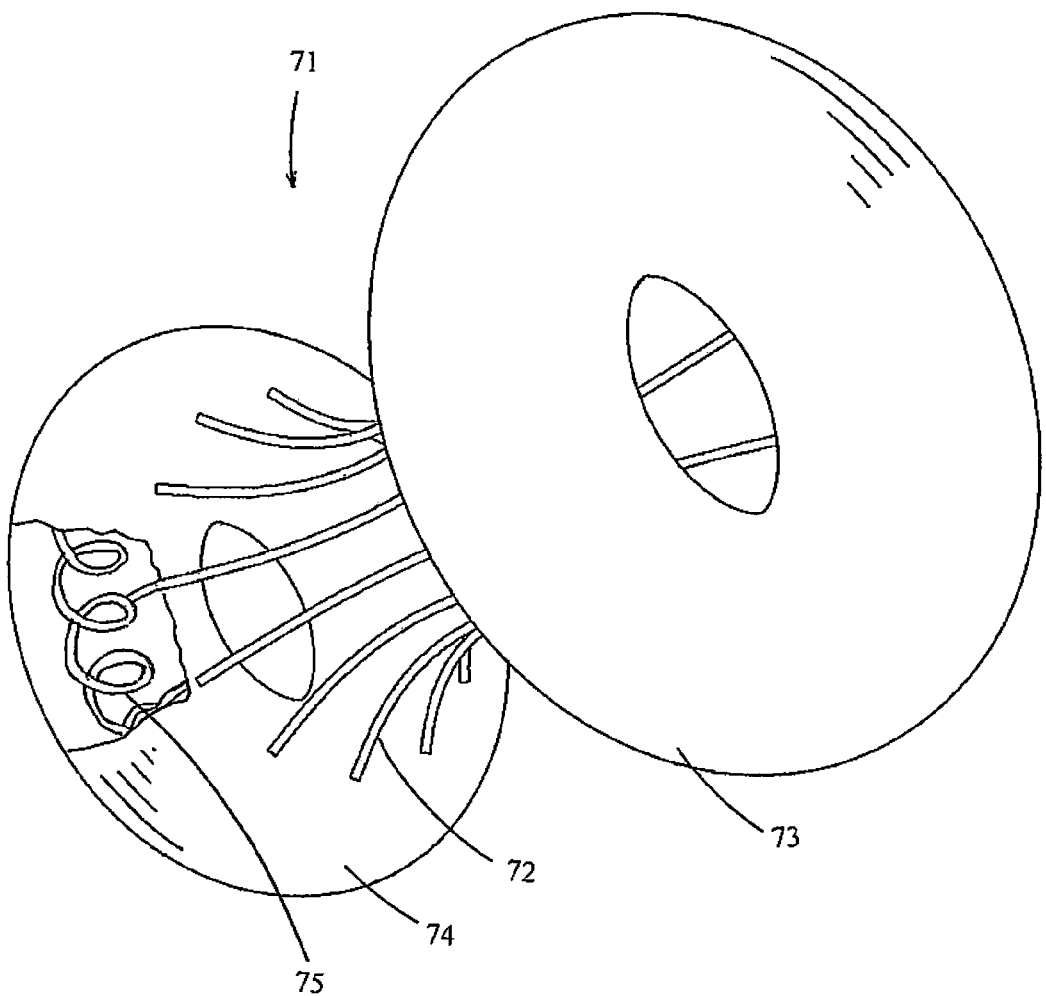
FIG. 14 shows a perspective view of the space filler device of FIG. 13.

FIGS. 13 and 14 show an intragastric space filler 71 with a shape retention mechanism made of different material as compared to the inflatable filler material. In one preferred embodiment, the space filler comprises two torus 73, 74. In another embodiment, the first torus space filler 73 and the second torus space filler 74 become one overall balloon-like space filler wrapped over the shape retention mechanism 72 and connected by the balloon-enclosed middle section 77. As shown in FIG. 14, the shape retention mechanism further comprises a spring-like coil 75 that is semi-compressible configured to resist compressive pressure from the stomach wall, but is flexible and collapsible by a retrievable instrument either through clamping, crimping, drawing string technique (as shown in FIG. 11) or other mechanical destructive methods. The shape retention mechanism may be made of Nitinol or other resilient, flexible metal or polymer.

A balloon-like space filler is generally manufactured by dip coating a mandrel into silicone solution a few times to build up the thickness. For connecting a balloon-like space filler with another space filler or safety element, silicone compatible adhesive is generally used, for example, RTV silicone or moderate temperature curing silicone adhesive.

In some embodiment, the safety element 22C comprises a pressure sensor element for sensing an internal pressure of the space filler 22A, wherein the pressure sensor element may further comprise a transmitter for wirelessly transmitting a measured internal pressure to a receiver outside a body of the patient. In one embodiment, the safety element comprises a pH sensor element for sensing a pH of a stomach of the patient, wherein the pH sensor element may further comprise a transmitter for wirelessly transmitting the sensed pH to a receiver outside a body of the patient. The sensed pH or the change of the sensed pH with respect to time is compared to the historic data or pre-determined data for assessing the device performance. If the sensed pH is below the threshold number for a predetermined period, this signal may prompt retrieval of the space filler device by a practitioner.

In one embodiment, the space filler and the safety element of the space filler device are configured to be in tandem inside a stomach pouch. In another embodiment, the space filler and the safety element are configured to be substantially parallel to each other. In a further embodiment, the safety element is anchored to or anchored through an inner wall of a stomach pouch.

In one embodiment, either the safety element or the space filler of the space filler device is ultrasonically visible. In another embodiment, an ultrasonic transducer is mounted on either the safety element or the space filler for emitting an ultrasonic signal.

In one embodiment, the gastric space filler device is configured to be deliverable through an esophagus of the patient. In another embodiment, at least a portion of an external surface of the space filler device is treated with an anti-acid substance, or an anti-adhesion substance. In a further embodiment, the space filler device has a central opening extending therethrough or the space filler is sized to occupy at least 90% of a stomach volume of the patient. In a further embodiment, the space filler has an adjustable volume and is sized and configured to occupy up to 90% of a stomach volume, preferably 95%, of the patient. The space filler should be able to be increased in size over time through port infusion or re-docking infusion. The size of the space filler can be adjusted over time to allow initial acceptance by the stomach and increased volume to get the right balance of weight loss and the lack of nausea and vomiting.

In one embodiment, the space filler device is fabricated from polyurethane sheet material, wherein the polyurethane sheet material comprises a single layer. In another embodiment, the space filler is made of a non-biodegradable material selected from a group consisting of polyester, polypropylene, Nylon, polyethylene, silicone, latex, polyethylene, and copolymers thereof. In one embodiment, the space filler device of the present invention is a permanent implant. In another embodiment, the space filler device of the present invention has a useful life of about 3 to 12 months.

In another embodiment, the safety element is an inflatable balloon made of a biodegradable material, wherein the biodegradable material is selected from a group consisting of polymers or copolymers of lactide, glycolide, caprolactone, polydioxanone, trimethylene carbonate, polyorthoesters, and polyethylene oxide. In another embodiment, the safety element is an inflatable balloon comprising a biodegradable material, wherein the biodegradable material is selected from a group consisting of collagen, chitosan, elastin, gelatin, and combinations thereof.

Figure 9:
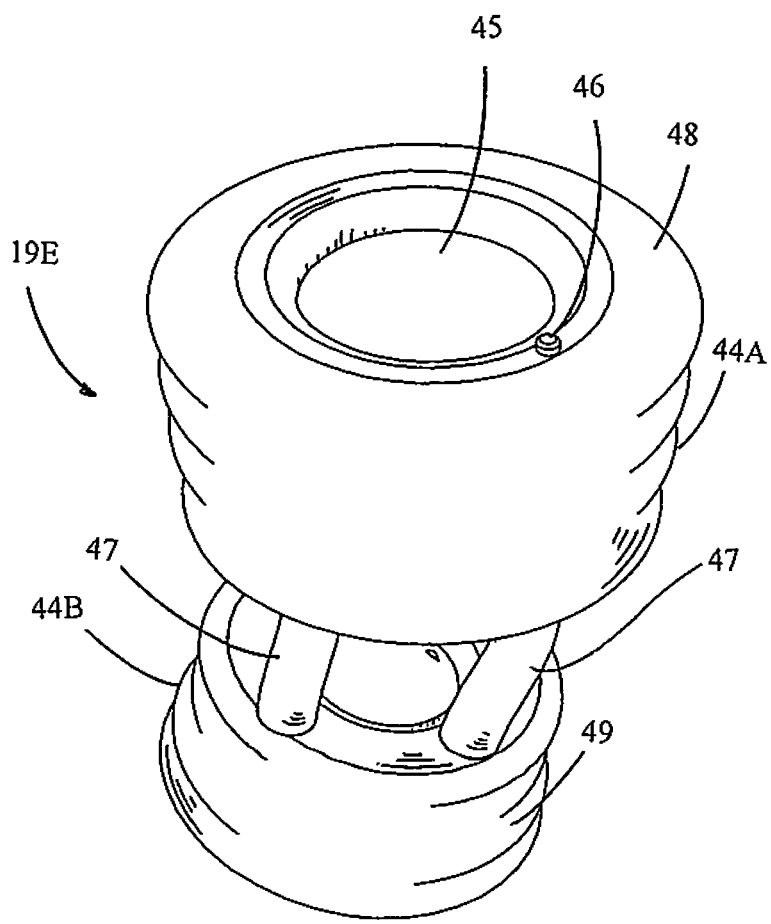
FIG. 9 shows one embodiment of a gastric space filler system with two connected expandable elements.
Figure 10:
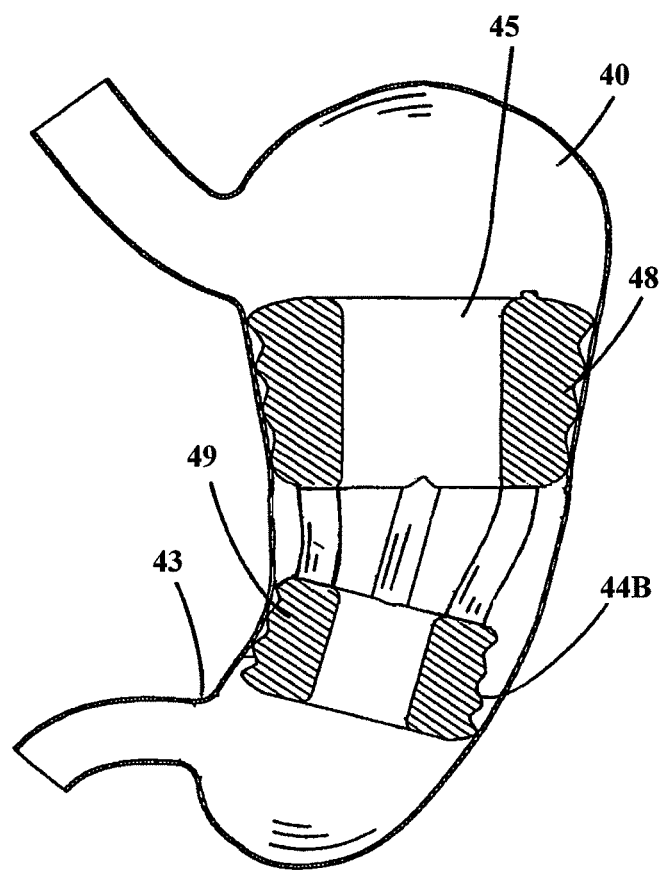
FIG. 10 shows an illustration of the gastric space filler system of FIG. 9 in a recipient.

FIG. 9 shows one embodiment of a gastric space filler device or system 19E with two connected expandable elements 48, 49 whereas FIG. 10 shows an illustration of the gastric space filler device of FIG. 9 in the stomach of a patient. The first expandable element 48 is connected to the second expandable element 49 with a plurality of connecting members 47. In one embodiment, the first expandable element 48 and the second expandable element 49 is not in fluid communication. In another embodiment, at least one of the connecting members 47 has a lumen therethrough for fluid communication between the two elements 48 and 49. Further, at least one of the expandable elements has a central passageway 45 for food pass-through.

The gastric space filler device 19E is sized and configured to fit the stomach volume up to 90% (preferably 95%) of the available stomach volume. In one embodiment, the peripheral surface 44A of the first element 48 and/or the peripheral surface 44B of the second element 49 is shaped like a corrugated shape so as to contact the inner wall of the stomach 40 at certain discrete lines (one dimension) of the corrugation, instead of contact areas (two dimensions). In one preferred embodiment, the second expanded element 49 is sized and shaped to distend against the inner wall of the stomach 40 at a place spaced away from the pylorus sphincter zone 43. In one embodiment, the second expanded element 49 comprises a plurality of smooth-surfaced convex protrusions disposed to permit engagement of the stomach wall by the space filler only at spaced localities, for minimizing mechanical trauma of the stomach wall by the space fillers.

Some aspects relate to an anchoring or securing mechanism of the space filler that anchors only when the space filler is adequately inflated. In one embodiment, at least one of the two space fillers of the gastric space filler system is anchored to an inner wall of the stomach. In a further embodiment, the anchoring action is arranged and configured to activate the anchoring mechanism (such as from a piercing needle) when the space filler is inflated while contacting the inner wall of the stomach, and to reverse the anchoring mechanism when the filler is deflated. The inflated space filler is maintained within or stabilized by anchoring or otherwise securing the expandable device to the stomach walls. In one embodiment, such expandable devices have tethering regions for attachment to the one or more fasteners which can be configured to extend at least partially through one or several folds of the patient's stomach wall. Such fasteners can be formed in a variety of configurations, e.g., helical, elongate, ring, clamp, and they can be configured to be non-piercing.

In one embodiment, at least a portion of an external surface of the space filler is treated with an anti-acid substance, corrosion-resistant substance or anti-adhesion substance, wherein the substance comprises polytetrafluoroethylene, inert material, or other biological material (such as albumin, melatonin, phosphorylcholine, immobilized antibody, or proteins) that are biocompatible. Methods of treating the surface include coating, painting, dipping, impregnation, and the like. In one embodiment, the melatonin or PC (phosphorylcholine) coating is on at least a portion of the outer surface of the space filler. In one preferred embodiment, the melatonin or phosphorylcholine coating is on at least the portion of the outer surface of the space filler that intends to contact the stomach wall. The stomach space filler may also be made of or surface coated with polyolefin family like high density polyethylene, linear low density polyethylene, and ultra high molecular weight polyethylene, fluoropolymer materials like fluorinated ethylene propylene, polymethylpentene, polysulphons, or some elastomers such as thermoplastic polyurethanes and C-Flex type block copolymers.

Melatonin may reduce the pain associated with irritable bowel syndrome (Gut 2005; 54:1402-1407). As is known to one ordinary skill in the art, melatonin is a sleep promoting agent that is involved in the regulation of gastrointestinal motility and sensation. In some prior clinical experiment, melatonin was orally administered 3 mg at bedtime for two weeks, those patients with melatonin regimen show significant attenuation in abdominal pain and reduced sensitivity in rectal pain as compared to the control group with placebo. Some aspects of the invention provide a gastric space filler device for treating obesity in a patient by reducing the stomach volume comprising an inflatable space filler and a safety element secured to the space filler, wherein the safety element yields a noticeable signal for causing a removal of the space filler, wherein at least a portion of an external surface of the space filler device is treated with melatonin.

PC is found in the inner and outer layers of cell membrane. However, it is the predominant component present in the outer membrane layer, and because it carries both a positive and negative charge (zwitterionic), it is electrically neutral. As a result, the outer layer of the cell membrane does not promote excess adhesion. When PC is coated on or incorporated on a material, protein and cell adhesion is decreased, inflammatory response is lessened, and fibrous capsule formation is minimized. Some aspects of the invention relate to a stomach space filler device coated with an immobilized antibody (such as CD34 or the like) that mimic a biological surface for less adhesion or less reactive. It is disclosed that a method of treating obesity in a patient with minimal nausea effects comprising implanting a stomach space filler device coated with an anti-nausea agent, wherein the anti-nausea agent may be melatonin, albumin or phosphorylcholine to mimic a biological surface.

Adjustable Intragastric Space Filler

The stomach space filler is capable of filling up to 95% of stomach, self-adjustable or portable. It may be dialed or programmed to adjust the space filler according to input signals of pressure, volume, pH, temperature, size, electrolyte properties, etc. In one embodiment, the space filler is also equipped with failure detection mechanism, such as bleeding/ulceration detection, migration limiter etc. The adjustable stomach space filler is retrievable. The device may be designed and arranged for restrictive food intake with custom shape that either adapts to or is made to the shape and size of a given patient's stomach.

Figure 12:
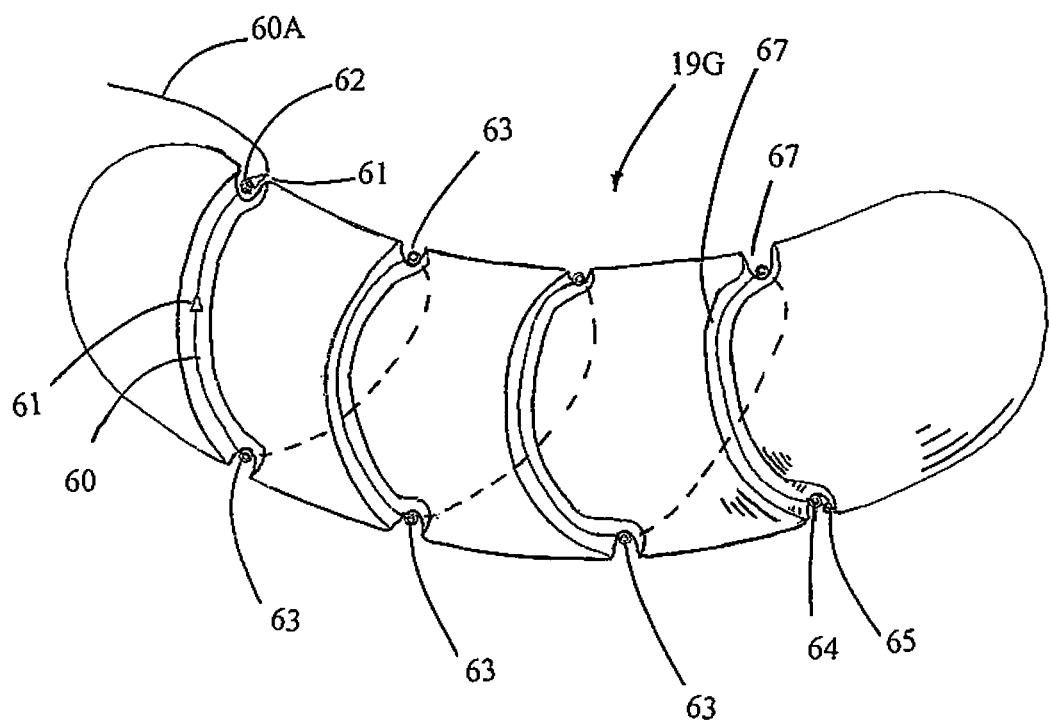
FIG. 12 shows an alternate embodiment of an adjustable space filler system.

FIG. 11 shows one embodiment of an adjustable space filler system 19F whereas FIG. 12 shows an alternate embodiment of an adjustable space filler system 19G. In one embodiment, the adjustable space filler comprises a drawstring 60 coupled to the plurality of rings 62, 63, 64 that are secured to the space filler 19F or 19G. In one embodiment, the rings may be an integral part of the space filler. A distal end-knot 65 of the drawstring 60 is sized larger than the opening of the distal ring 64. The distal end-knot keeps the distal end of the drawstring snugly tight around the distal ring secured on the space filler. When the proximal section 60A of the drawstring is pulled away from the space filler through the proximal ring 62, the space filler becomes smaller radially or spirally. In one embodiment, a conical shaped blocker 61 can pass the ring in a one-way manner. Therefore, the volume of the space filler becomes smaller each time a conical shaped blocker passes the proximal ring 62. To make the space filler with less profile, a trough 67 may be sized and configured to allow the drawstring 60 and the rings 62, 63, 64 not to protrude beyond the outermost external surface of the space filler 19G (as shown in FIG. 12).

From the foregoing, it should now be appreciated that a gastric space filler device comprising at least two space fillers with at least one space filler is partially biodegradable has been disclosed. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A gastric space filler device for treating obesity in a patient by reducing the patient's stomach volume, the gastric space filler device comprising:
   a plurality of inflatable gastric space fillers including at least a first inflatable gastric space filler and a second inflatable gastric space filler;
   a plurality of connecting members extending between and connected to the first and second inflatable gastric space fillers such that the first and second inflatable space fillers are arranged in tandem when in the patient's stomach, wherein opposing ends of the first and second inflatable gastric space fillers are spaced apart from each other by the connecting members; and
   a safety element configured to yield a noticeable signal for causing a removal of the gastric space filler device from the patient;
   wherein the gastric space filler device approximates a natural J-shape of a stomach of the patient and is sized to occupy at least 90% of the patient's stomach volume to reduce stomach volume for weight loss.

2. The gastric space filler device of claim 1, wherein the safety element is a pressure sensor element configured to sensing an internal pressure of at least one of the first inflatable gastric space filler and the second inflatable gastric space filler.

3. The gastric space filler device of claim 2, wherein the pressure sensor element includes a transmitter configured to wirelessly transmitting the sensed internal pressure to a receiver outside a body of the patient.

4. The gastric space filler device of claim 1, wherein the safety element includes a pH sensor element for sensing a pH of a stomach of the patient.

5. The gastric space filler device of claim 4, wherein the pH sensor element includes a transmitter for wirelessly transmitting the sensed pH to a receiver outside a body of the patient.

6. The gastric space filler device of claim 1, wherein the safety element is anchored to an inner wall of a stomach of the patient.

7. The gastric space filler device of claim 1, wherein the safety element and/or at least one of the first and/or second inflatable gastric space fillers are ultrasonically visible.

8. The gastric space filler device of claim 1, further comprising an ultrasonic transducer configured to emit an ultrasonic signal.

9. The gastric space filler device of claim 1, wherein the gastric space filler device is configured to be deliverable through an esophagus of the patient.

10. The gastric space filler device of claim 1, wherein at least a portion of an external surface of the gastric space filler device is treated with an anti-acid substance.

11. The gastric space filler device of claim 1, wherein at least a portion of an external surface of the gastric space filler device is treated with a corrosion-resistant substance.

12. The gastric space filler device of claim 1, wherein at least a portion of an external surface of the gastric space filler device is treated with an anti-adhesion substance.

13. The gastric space filler device of claim 1, wherein at least a portion of an external surface of the gastric space filler device is treated with albumin or melatonin.

14. The gastric space filler device of claim 1, wherein at least a portion of an external surface of the gastric space filler device is treated with phosphorylcholine.

15. The gastric space filler device of claim 1, wherein the inflatable space filler includes a central opening extending therethrough.

16. The gastric space filler device of claim 1, wherein at least one of the first and/or second inflatable gastric space fillers has an adjustable volume.

17. The gastric space filler device of claim 1, wherein the first and second inflatable gastric space fillers include a volume-adjusting mechanism for adjusting a volume of the inflatable space filler over time, wherein the volume-adjusting mechanism adjusts the volume to a first volume configured to allow initial acceptance by a stomach of the patient, and wherein the volume-adjusting mechanism increases the volume to a second volume configured to induce weight loss and minimize nausea and vomiting.

18. The gastric space filler device of claim 1, wherein the safety element is an inflatable balloon made of a biodegradable material.

19. The gastric space filler device of claim 1, wherein the safety element is secured to the first and/or second inflatable gastric space fillers.

20. The gastric space filler device of claim 1, wherein the safety element is one of the first and/or second inflatable gastric space fillers.

21. The gastric space filler device of claim 1, wherein the first inflatable gastric space filler is configured to be inflated to a first volume in a stomach of the patient and the second inflatable gastric space filler is configured to be inflated to a second volume inside the stomach of the patient, and wherein the first volume and the second volume are configured to occupy at least 90% of the stomach volume.

22. The gastric space filler device of claim 1, further comprising:
   an infusing tube releasably attached to the gastric space filler device, wherein the infusing tube is configured to be connected to an external fluid source to inflate the inflatable gastric space fillers when the inflatable gastric space fillers are positioned within a stomach of the patient, and wherein the infusing tube is removed from the patient after inflation.

23. An inflatable gastric device, comprising:
a first inflatable space filler;
a second inflatable space filler arranged in tandem with the first inflatable space filler;
a connecting member extending between and connected to the first and second inflatable space fillers, wherein opposing ends of the first and second inflatable space fillers are spaced apart from each other by the connecting member; and
a safety element configured to yield a noticeable signal of failure of the inflatable gastric device,
wherein the first inflatable space filler, the second inflatable space filler, and the connecting member are sealed from fluid passage through the inflatable gastric device after inflation of the first and second inflatable space fillers, and
wherein, after inflation of the first and second inflatable space fillers, the inflatable gastric device approximates a natural J-shape of a stomach of a human patient and is sized to occupy at least 90% of a stomach volume to reduce stomach volume for weight loss of the human patient.

24. The inflatable gastric device of claim 23, wherein the safety element is a pressure sensor element coupled to at least one of the first inflatable space filler and the second inflatable space filler.

25. The inflatable gastric device of claim 23, wherein the safety element is secured to the first and/or second inflatable space fillers.

26. The inflatable gastric device of claim 23, wherein the safety element is one of the first and/or second inflatable gastric space fillers.

27. The inflatable gastric device of claim 26, wherein the safety element includes a dye.

28. The inflatable gastric device of claim 23, further comprising:
an infusing tube releasably attached to the inflatable gastric device, wherein the infusing tube is configured to extend from a stomach of a patient and through a mouth of the patient to connect with an external fluid source, and wherein the infusing tube is configured to be removed the patient after inflation such that the inflatable gastric device is completely positioned within the stomach of the patient.

29. The inflatable gastric device of claim 23, wherein the safety element is a pressure sensor element configured to sensing an internal pressure of at least one of the first inflatable gastric space filler and the second inflatable gastric space filler, and wherein the pressure sensor element includes a transmitter configured to wirelessly transmitting the sensed internal pressure to a receiver outside a body of the patient.

30. The inflatable gastric device of claim 23, wherein the safety element includes a pH sensor element for sensing a pH of a stomach of the patient, and wherein the pH sensor element includes a transmitter for wirelessly transmitting the sensed pH to a receiver outside a body of the patient.

31. The inflatable gastric device of claim 23, wherein the safety element is anchored to an inner wall of a stomach of the patient.

32. The inflatable gastric device of claim 23, further comprising an ultrasonic transducer configured to emit an ultrasonic signal.

33. The inflatable gastric device of claim 23, wherein the gastric space filler device is configured to be deliverable through an esophagus of the patient.

34. The inflatable gastric device of claim 23, wherein at least a portion of an external surface of the gastric space filler device is treated with at least one of anti-acid substance, a corrosion-resistant substance, an anti-adhesion substance, albumin, melatonin, phosphorylcholine.

35. The inflatable gastric device of claim 23, wherein the first and second inflatable space fillers include a central opening extending therethrough.

36. The inflatable gastric device of claim 23, wherein at least one of the first and/or second inflatable space fillers has an adjustable volume.

37. The inflatable gastric device of claim 23, wherein the first and second inflatable space fillers include a volume-adjusting mechanism for adjusting a volume of the inflatable space filler over time, wherein the volume-adjusting mechanism adjusts the volume to a first volume configured to allow initial acceptance by a stomach of the patient, and wherein the volume-adjusting mechanism increases the volume to a second volume configured to induce weight loss and minimize nausea and vomiting.

38. The inflatable gastric device of claim 23, wherein the safety element is an inflatable balloon made of a biodegradable material.

39. An inflatable gastric device, comprising:
a first inflatable space filler;
a second inflatable space filler arranged in tandem with the first inflatable space filler;
a connecting member extending between and connected to the first and second inflatable space fillers, wherein opposing ends of the first and second inflatable space fillers are spaced apart from each other by the connecting member; and
a safety element configured to yield a noticeable signal of failure of the inflatable gastric device,
wherein the first inflatable space filler, the second inflatable space filler, and the connecting member are sealed from fluid passage through the inflatable gastric device after inflation of the first and second inflatable space fillers, and
wherein, after inflation of the first and second inflatable space fillers, the inflatable gastric device tends to assume a natural curved shape of a stomach of a human patient and is sized to occupy at least 90% of a stomach volume of the human patient.

* * * * *